US011791047B2

(12) United States Patent
Paris et al.

(10) Patent No.: US 11,791,047 B2
(45) Date of Patent: *Oct. 17, 2023

(54) MEDICATION RECOMMENDATION SYSTEM AND METHOD FOR TREATING MIGRAINE

(71) Applicant: HEALINT PTE. LTD., Singapore (SG)

(72) Inventors: Nicholas Laurent Paris, Singapore (SG); Francois Jean Sebastien Cadiou, Singapore (SG); Christophe Perret, Singapore (SG)

(73) Assignee: HEALINT PTE. LTD., Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 17/661,227

(22) Filed: Apr. 28, 2022

(65) Prior Publication Data

US 2022/0254494 A1 Aug. 11, 2022

Related U.S. Application Data

(63) Continuation of application No. 17/302,796, filed on May 12, 2021, now Pat. No. 11,355,243, which is a continuation of application No. PCT/IB2019/059692, filed on Nov. 12, 2019.

(30) Foreign Application Priority Data

Nov. 12, 2018 (GB) ..................... 1818360

(51) Int. Cl.
*G16H 50/20* (2018.01)
*G16H 20/10* (2018.01)
*G16H 80/00* (2018.01)

(52) U.S. Cl.
CPC ............. *G16H 50/20* (2018.01); *G16H 20/10* (2018.01); *G16H 80/00* (2018.01)

(58) Field of Classification Search
CPC ......... G16H 50/20; G16H 20/10; G16H 80/00
(Continued)

(56) References Cited

U.S. PATENT DOCUMENTS

2011/0184250 A1* 7/2011 Schmidt .................. G16Z 99/00
600/300
2013/0095459 A1* 4/2013 Tran ....................... G09B 19/00
434/247
(Continued)

FOREIGN PATENT DOCUMENTS

WO 2016037055 A1 3/2016
WO WO-2016037055 A1 * 3/2016 .............. G06F 17/11

OTHER PUBLICATIONS

S. Mohan and A. Mukherjee, "MigraineCloud," SoutheastCon 2018, 2018, pp. 1-7, doi: 10.1109/SECON.2018.8478869 (Year: 2018).*
(Continued)

*Primary Examiner* — Joy Chng
(74) *Attorney, Agent, or Firm* — Craige Thompson; Thompson Patent Law; Timothy D. Snowden

(57) ABSTRACT

Method and System for providing a medical drug recommendation. Time and location data is read from received client data. Weather data is retrieved based on the time and location data and the weather data is stored in a user data set. A medical drug recommendation is computed from a user data set that comprises migraine event data by using a statistical model. Furthermore, a server is prepared to provide medical drug recommendations, wherein a statistical model for delivering a medical drug recommendation is adjusted by providing user data as input data to a statistical model, the user data sets comprising migraine events.

26 Claims, 18 Drawing Sheets

Figure 1:
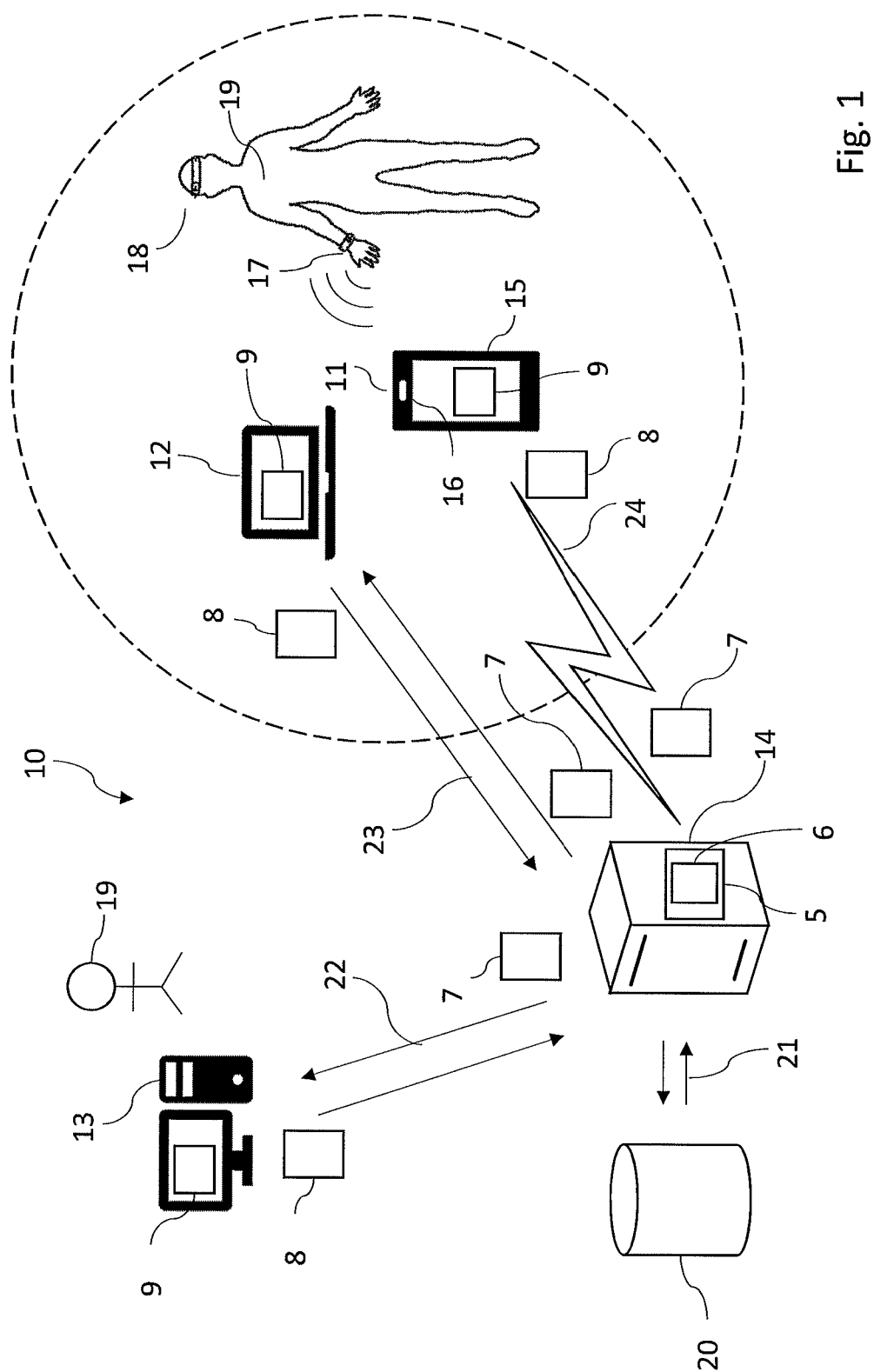

(58) Field of Classification Search
USPC .......................................................... 705/2–3
See application file for complete search history.

(56) References Cited

U.S. PATENT DOCUMENTS

| | | | |
|---|---|---|---|
| 2018/0096107 A1* | 4/2018 | Demestichas | G16H 50/70 |
| 2018/0102187 A1 | 4/2018 | Apte et al. | |
| 2018/0344238 A1* | 12/2018 | Pastuhov | A61B 5/117 |
| 2020/0121544 A1* | 4/2020 | George | A61H 9/00 |

OTHER PUBLICATIONS

Muoio, MobiHleathNews.com, Machine Learning App Migraine Alert Warns Patients Of Oncoming Episodes, Oct. 30, 2017, http://https://www.mobihealthnews.com/content/machine-learning-app-migraine-alert-warns-patients-oncoming-episodes (Year: 2017).*
Applicant Response with Amended Claims in related Foreign Application No. GB1818360.8, dated Aug. 23, 2019, 20 pages.
Examination Opinion in related Foreign Application No. GB1818360.8, dated Apr. 26, 2019, 7 pages.
Examiner Response in related Foreign Application No. GB1818360.8, dated Sep. 24, 2019, 2 pages.
International Search Report in related PCT Application No. PCT/IB2019/059692, dated Jan. 23, 2020, 4 pages.
Telephone Conversation Report in related Foreign Application No. GB1818360.8, dated May 23, 2019, 1 page.
Written Opinion in related PCT Application No. PCT/IB2019/059692, dated Jan. 23, 2020, 6 pages.

* cited by examiner

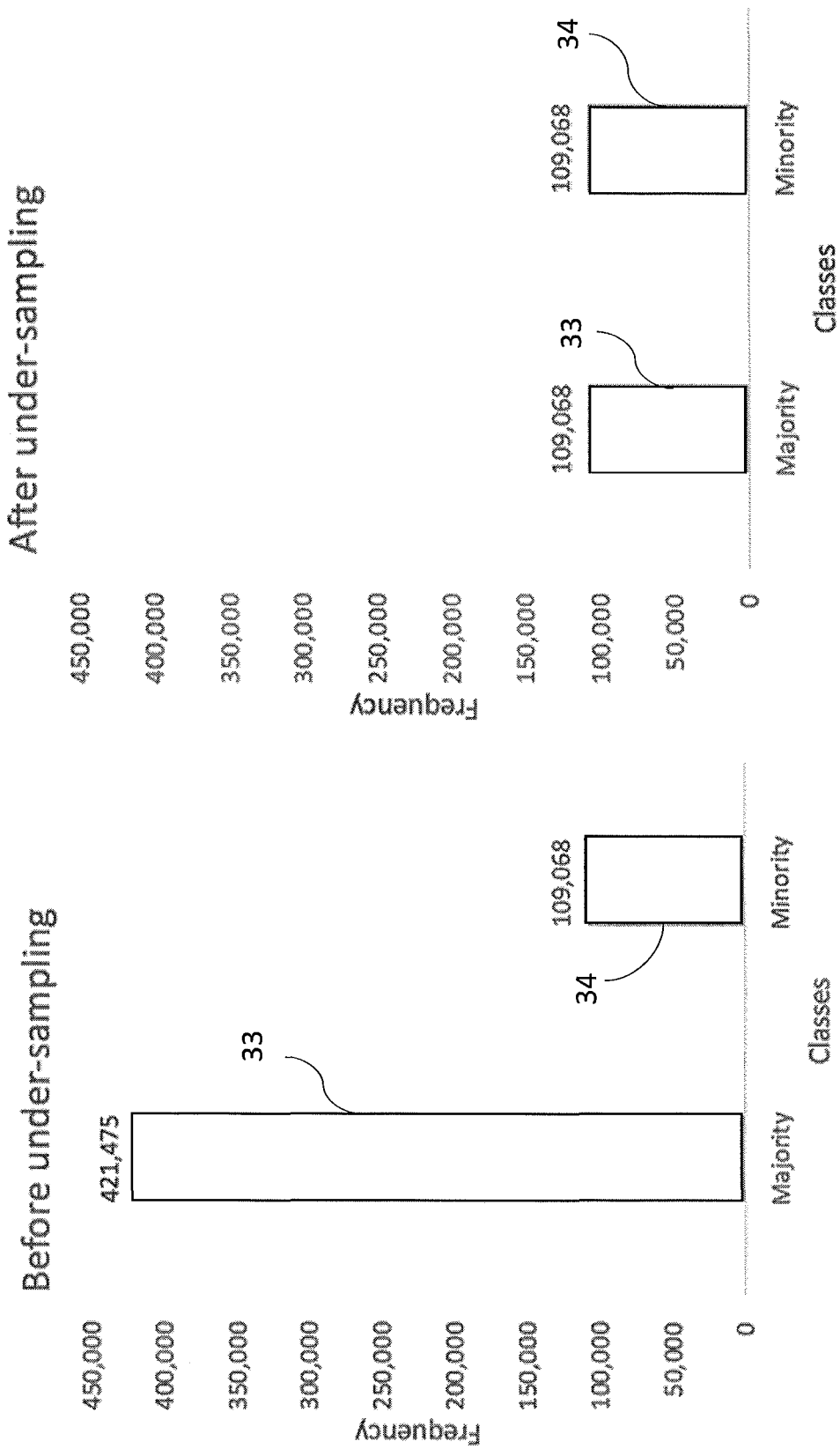

| User# | Excluded medication# |
|---|---|
| 1 | 20, 23, 25 |
| 1 | 21 |
| 2 | 18 |
| 3 | -- |
| 4 | -- |

42

43

| Medication# | Name | Active content mg | Complication# | Indication# | Provider # | Previous success rate (%) |
|---|---|---|---|---|---|---|
| 1 | Sumatriptan | 75 | 3;4;5 | 1;2 | 1 | 50 |
| 2 | Erenumab | 60 | 2;10 | 1;2;3 | 7 | 60 |
| 3 | Frovatriptan | 52 | 2 | 1;2;4 | 6 | 65 |
| 4 | Zolmitriptan | 40 | -- | 1;3 | 3 | 70 |
| 5 | Galcanezumab | 33 | 2;10 | 1;3;4 | 3 | 45 |

Fig. 23

MEDICATION RECOMMENDATION SYSTEM AND METHOD FOR TREATING MIGRAINE

CROSS-REFERENCE TO RELATED APPLICATIONS

This application is a Continuation of and claims the benefit of U.S. application Ser. No. 17/302,796, titled "MEDICATION RECOMMENDATION SYSTEM AND METHOD FOR TREATING MIGRAINE," filed by Nicholas Laurent Paris, et al. on May 12, 2021, which application is a Continuation of and claims the benefit of PCT Application Serial No. IB2019/059692, titled "MEDICATION RECOMMENDATION SYSTEM AND METHOD FOR TREATING MIGRAINE," filed by HEALINT PTE. LTD. on Nov. 12, 2019, which application claims priority to United Kingdom Application Serial No. GB 1818360.8, titled "MEDICATION RECOMMENDATION SYSTEM AND METHOD FOR TREATING MIGRAINE," filed by HEALINT PTE. LTD. on Nov. 12, 2018.

This application incorporates the entire contents of the foregoing application(s) herein by reference.

The present specification relates to an automated drug recommendation system.

Migraine is a prevalent neurological disease, affecting 39 million people in the United States and 1 billion worldwide (Migraine Research Foundation (2018)). However, according to the same information source there are fewer than 500 certified headache specialists in the United States. In situations in which there is a scarcity of migraine-related medical resources and a disproportion between specialized doctors and patients this can lead to prolonged waiting times for appointments, to difficulties in migraine diagnosis and failure to prevent and treat migraines. With rising awareness of physical health and development of technology on the other hand, people are increasingly motivated to track their health statistics using smart devices.

The present specification provides an improved medication recommender, an improved method for providing a medication recommendation and an improved system for providing the medication recommendation, in particular for people affected by migraine.

In a first aspect, the current specification provides a method, and a server device for providing an improved recommended medication to a user. Among others, this provides a solution to the technical problem of improving a prediction accuracy of a migraine prediction model with the aid of user input data relating to migraine events, and pressure data.

Further input data such as other environment data gained by environment sensor or sensors measuring a user body condition can also be used to improve prediction accuracy. Furthermore, a solution is provided to obtain weather data, and especially pressure data, by using time and location data from a client device and retrieving the corresponding pressure data from a weather server. The location data can be obtained by using a location sensor of the client device, for example a satellite navigation system, such as GPS, or a receiver of location messages of a communication network and the location data can be obtained by a computer clock of the client device. A pressure condition can contribute to a migraine event and is thereby useful to improve a prediction accuracy of a statistical model.

According to this method, a computer readable program is executed or run on a server. In other words, the method is a computer implemented method, which is implemented by the computer readable program. Among others, the computer readable comprises a statistical model and a model adjuster for adjusting the statistical model.

The program receives client data from a client application that is installed on a client device, such as a mobile phone or other mobile computing device. The client data comprises time data and location data. The location data indicates a position of a client device of a user of the client device, and the time data indicates an onset of a migraine event of the user. The time data can be input by the user or it can also be determined by means of a sensor.

Furthermore, the program sends a data retrieval message to a weather data server. In one embodiment, the weather data server comprises a database with weather data. The data retrieval message comprises the previously received time data and location data.

The weather data server retrieves weather data that corresponds to the time data and the location data, for example by comparing the time data and the location data with values in the weather database.

Furthermore, the computer readable program receives the weather data from the weather data server. In particular, the weather data comprises atmospheric pressure data that corresponds to the time data and the location data, and which is useful to as migraine event data to predict an outcome when a medication is provided to the user.

The computer readable program creates a user data set which comprises the client data and atmospheric pressure data. Furthermore, the computer readable program generates a recommended medication based on the client data and the atmospheric pressure data using the statistical model and outputs a recommendation message to the client device of the user. The recommendation message comprising the recommended medication.

In a further step, the computer readable program sends a request message to the client device. The request message contains a first question whether the user took a medication according to the recommendation message, and a second question whether the medication was successful.

In a later step, the computer readable program receives a response message to the request message from the client device.

If the response message indicates that the medication was not successful: the recommendation that was provided to the client device (11, 12, 13) is stored. Thereby, is prevented that the client device receives the same medication twice.

Furthermore, the statistical model is adjusted based on the response message such that a prediction accuracy of the statistical model is improved. Thereby, the user feedback whether a recommended medication was successful or not can be used to adjust and thereby improve the statistical model.

This adjustment of the statistical model can be carried out after every feedback of the user or multiple user feedbacks can be stored first and an adjustment of the model can be carried out when a specified number of user feedbacks has been reached. The adjustment of the statistical model can refer to the adjustment of parameters of the statistical model, such as split criteria of a decision tree or weights of a neuronal network. The adjustment can also refer to rebuilding the statistical model "from scratch" when the adjustment is run.

Furthermore, the method can also comprise the steps of providing a sample database that is connected to the server or stored on the server. The database comprises user data sets which in turn comprise migraine event data, an applied recommendation, and an outcome. Furthermore, the database can also comprise user data sets which comprise migraine event data of an ongoing migraine event. These user data sets do not yet comprise an applied recommendation and an outcome.

According to a specific embodiment, the statistical model of the computer readable program comprises a decision tree. Furthermore, the method comprises an adjusting of the statistical model that comprises the decision tree.

In particular, the adjusting of the statistical comprises generating a training database from a database, that comprises user data sets with migraine event data. The user data sets comprise migraine event data which are contained in the previously received client data and an outcome from the previously received response message. For example, the training database can be obtained by randomly drawing or sampling a predefined number of user data sets from the database.

The outcome indicates whether the recommended medication was successful. Furthermore, the database can comprise previously stored user data sets with migraine event data.

Starting from a root node, the training database, or rather the decision tree represented by the training database, is split into two branches using a decision rule and thereby generating a new child node for each of these two branches, wherein the decision rule is chosen to maximize an information gain.

For each new child node, the splitting is repeated until the training database cannot be split any further.

According to a further specific embodiment of the method, the statistical model comprises a decision tree and the method comprises an adjusting of the statistical model that comprises the decision tree.

The adjusting of the statistical model comprises adjusting values of branching criteria of nodes of the decision tree based on the client data and on an outcome from the response message, wherein the outcome indicates whether the recommended medication was successful.

According to a further specific embodiment of the method, the statistical model comprises a decision tree and wherein the method comprises an adjusting of the statistical model. According to this method the statistical model is adjusted by adding and/or removing branches to the decision tree based on the client data and on an outcome from the response message, where the outcome indicates whether the recommended medication was successful. This embodiment can be combined with the previous embodiment, in which values of the branching criteria are adjusted.

According to a further specific embodiment of the method, the statistical model comprises a random forest and the method comprises an adjusting of the statistical model comprises generating a new random forest, as compared to adjusting a pre-existing random forest.

The adjusting of the statistical model comprising generating a training database and a test database from a database. The database comprises user data sets with migraine event data that contained in the client data and an outcome from the response message, wherein the outcome indicates whether the recommended medication was successful, Furthermore the database can comprise previously stored user data sets which may come from various data sources, such as clinical trials or otherwise. The test database as well as the training database can be obtained by random sampling a predefined number of data sets with or without replacement.

Then, a random forest is generated using the training database and measuring the statistical model accuracy on the test database. Among other, the measured model accuracy can be used for a decision on whether to retain the generated random forest or to repeat the process of generating the test database and generating the random forest.

According to a further specific embodiment of the method, the statistical model comprises a gradient boosting trees model, the method comprises an adjusting of the statistical model and the adjusting of the statistical model comprises generating a training database from a database, the database comprising user data sets. The user data sets comprising migraine event data, which are contained in the client data and an outcome from the response message that indicates whether the recommended medication was successful. Furthermore, the database can also comprise previously stored user data sets.

A statistical model is fitted to the training database, and a difference or residual between a predicted output of the statistical model and training database ground truth is computed. For example, the ground truth can be provided by the outcomes in the training database.

A new model is fitted to the computed difference, and an improved statistical model as a sum of the statistical model and the new model. The steps of computing a difference between a predicted output of the statistical model and the training database, fitting a new model to the computed difference, and obtaining an improved statistical model as a sum of the previously computed statistical model and the new model are repeated.

The repetition of the steps can be carried out until a difference is between a predicted output of the statistical model and the training database is lower than a predefined difference.

According to a further specific embodiment of the method, the method comprises a gradient boosting trees model, and the method comprises an adjusting of the statistical model, which comprises generating a training database from a database, wherein the database comprises user data sets with migraine event data. The migraine event data which are contained in the client data. Furthermore, the user data sets each comprise an outcome from the response message, which indicates whether the recommended medication was successful. Furthermore, the database can comprise previously stored user data sets.

A sequence of decision trees is generated by the following steps: a first decision tree to the training database, an output of the decision tree is computed using the training database, and a difference between the training database (33) and the output of the decision tree is computed.

Furthermore, a loss function is computed from the difference and a gradient of the loss function is computed. Then, a further decision tree is computed using the gradient of the loss function and an improved statistical model is obtained as a sum of the outputs of the previously computed first decision tree and the further decision tree.

Until a pre-determined accuracy of prediction is reached, the steps following steps are repeated: A difference is computed between the training database, and the output of the decision tree, a loss function is derived from the difference, and a a gradient of the loss function is computed. Moreover, a further decision tree is computed using the gradient of the loss function, and an improved statistical model as a sum of the outputs of the previously computed decision trees and the further decision tree.

According to a further embodiment of the method, which handles a time overlap between reported migraine events, second client data are received from a client device, a first user identification data is derived from the previously received client data and a second user identification data is derived from the second client data.

If the second user identification is identical to the first user identification a first migraine event start time and a first migraine event end time is derived from the previously received client data, and a first migraine event start time and a first migraine event end time. It is determined whether there is a time overlap between a first migraine event having the first migraine event start time and the first migraine event end time and a second migraine event having the second migraine event start time and the first migraine event end time.

If it is determined that there is a time overlap between the first migraine event and the second migraine event, a data collision rule that prevents that two separate user data sets are generated for the second migraine event and the first migraine event is applied. For example, the data collision rule can decide that a first entry wins or that the data from the two migraine events is merged.

In a second aspect, which is related to the first aspect, the specification discloses a server for providing a migraine medical drug recommendation. The server comprises a computer readable program in a computer readable memory of the server.

The computer readable program is operative to receive client data from a client application, wherein the client data (8) comprises time data and location data. The location data indicates a position of a client device of a user, and the time data indicating an onset of a migraine event of the user.

Furthermore, the program is operative to send a data retrieval message to a weather data server. The weather data server comprises a database with weather data, and the data retrieval message comprises the time data and the location data. This causes the weather data server to retrieve weather data that corresponds to the timestamp data and the location date.

Furthermore, the computer readable program is operative to receive weather data from the weather data server, wherein the weather data comprising atmospheric pressure data that corresponds to the time data and the location data. The computer readable program is also operative to create a user data set that comprises the client data and atmospheric pressure data, and to generate a recommended medication based on the client data and the atmospheric pressure data using the statistical model, and to output a recommendation message to the user of the client device, wherein the output message comprises the recommended medication.

Furthermore, the computer readable program is operative to send a request message to a client device of a user. The client device comprises an application that is installed for a user, and hence provides identification data of the user. By making use of the identification data, the request message is sent to the same user to which the medication was previously provided.

The request message contains a first question whether the user took a medication according to the recommendation message, and a second question whether the medication was successful. Furthermore, the computer readable program is operative to receive a response message to the request message from the client device to which the request message was sent.

If the response message indicates that the medication was not successful the computer readable program stores the recommendation that was provided to the client device, and thereby prevents that the client device receives the same medication twice.

Furthermore, the computer readable program is operative to adjust the statistical model based on the response message, such that a prediction accuracy of the statistical model is improved.

According to a further embodiment of a server, the statistical model of the computer readable program on the server comprises a decision tree. Furthermore, the computer readable program is operative to adjust the statistical model. The adjusting of the statistical model comprises generating a training database from a database, the database comprising user data sets with migraine event data. The migraine event data are contained in previously received client data and have been stored in the user data sets. Furthermore, the user data sets each comprise an outcome which was previously received in the response message (8) and is now stored in the respective user data set. The outcome indicates whether the recommended medication was successful. Furthermore, the database can also comprise previously stored user data sets which were not obtained via response messages and client data but by other means.

The computer readable program is operative to split, starting from a root node, the training database into two branches using a decision rule and thereby generating a new child node for each of these two branches, wherein the decision rule is chosen to maximize an information gain. For each new child node, the splitting is repeated until the training database cannot be split any further.

According to a further embodiment of the server, the statistical model comprises a decision tree and the computer readable program installed on the server is furthermore operative to adjust the statistical model.

The adjusting of the statistical model comprises adjusting values of branching criteria of nodes of the decision tree based on the client data and on an outcome from the response message, wherein the outcome indicates whether the recommended medication was successful. Furthermore, the criteria of predetermined nodes of the decision tree can also be adjusted based on a training database.

According to a further embodiment of the server, the statistical model comprises a decision tree and the computer readable program is operative to adjust the statistical model.

The adjusting of the statistical model comprises adding and/or removing branches to the decision tree based on the client data and on an outcome from the response message, the outcome indicating whether the recommended medication was successful.

According to a further embodiment of the server, the statistical model comprises a random forest and the computer readable program is operative to adjust the statistical model.

The adjusting of the statistical model comprises generating a training database and a test database from a database that comprises user data sets with migraine event data. the user data sets comprise migraine event data contained in the client data and an outcome from the response message, wherein the outcome indicates whether the recommended medication was successful. Furthermore, the database can comprise previously stored user data sets. The computer readable program is furthermore, operative generate a random forest using the training database and measuring the statistical model accuracy on the test database.

In a further embodiment, of the server, the statistical model comprises a gradient boosting trees model. The computer readable program is operative to adjust the statistical model And the adjusting of the statistical model comprises the following steps Generating a training database from a database, the database comprising user data sets, the user data sets comprising migraine event data, which are contained in the client data and an outcome from the response message, the outcome indicating whether the recommended medication was successful.

A statistical model is fitted to the training database, and a difference or residual between a predicted output of the statistical model and a ground truth of the training database ground truth is computed.

A new model is fitted to the computed difference, and an improved statistical model as a sum of the statistical model and the new model.

Until a predetermine difference or prediction accuracy is reached the following steps are repeated. A difference between a predicted output of the statistical model and the training database is computed, a new model is fitted to the computed difference, and an improved statistical model is obtained as a sum of the previously computed statistical model and the new model.

In a further embodiment of the server, the statistical model comprises a gradient boosting trees model, and wherein the computer readable program on the server is operative to adjust the statistical model, and the adjusting of the statistical model comprises:

generating a training database from a database, the database comprising user data sets, the user data sets comprising migraine event data which are contained in the client data and an outcome from the response message, the outcome indicating whether the recommended medication was successful.

Generating a sequence of decision trees by the following steps: fitting a first decision tree to the training database, computing an output of the decision tree using the training database, computing a difference between the training database (33) and the output of the decision tree deriving a loss function from the difference, and computing a gradient of the loss function. Furthermore, a further decision tree is computed using the gradient of the loss function, and an improved statistical model as a sum of the outputs of the previously computed first decision tree and the further decision tree. These steps are repeated until until a predetermined accuracy of prediction is reached.

In a further embodiment of the server, the computer readable program is further operative to receive second client data from a client device, to derive first user identification data from the previously received client data and to derive second user identification data from the second client data. If the second user identification is identical to the first user identification, a first migraine event start time and a first migraine event end time is derived from the previously received client data and a first migraine event start time and a first migraine event end time is derived from the second client data.

It is determined, whether there is a time overlap between a first migraine event having the first migraine event start time and the first migraine event end time and a second migraine event having the second migraine event start time and the first migraine event end time, and, if the computer readable program determines that there is a time overlap between the first migraine event and the second migraine event, a data collision rule is applied that prevents that two separate user data sets are generated for the second migraine event and the first migraine event.

In a further aspect, the specification discloses a method for preparing a server to provide a migraine medical drug recommendation or suggestion message in that pre-existing data are used to generate a statistical model, such that users of client devices can start using the statistical model and receiving recommendations. Furthermore, the statistical model can then be further improved with the user feedbacks, as described further above.

A database is provided, which is connected to a server. The database comprises user data sets, and each user data set comprises migraine event data, an applied recommendation, and an outcome. The migraine event data comprises time data and location data. Furthermore, a computer readable program is provided or installed on the server.

The computer readable program comprises a statistical model and a statistical model adjuster for adjusting the statistical model base on input provide to the statistical model adjuster.

When the computer program is run, it causes a partitioning of the database into a training data base and a test data base, for example by determining data set sizes and random sampling of user data sets with or without replacement, each comprising user data sets.

The training database is provided as input data to the statistical model adjuster, and a statistical model is built or generated based on the training database by using the statistical model adjuster. Therein, a generation of the model is also a form of adjusting the statistical model.

The test database is provided as input to the statistical model, the statistical model is evaluated based on the test database, wherein evaluating refers to the generation of predictions of outcomes with the statistical model.

The adjusting of the statistical model can also comprise adjusting parameters of the statistical model based on the input data, to obtain an adjusted statistical model, such that a prediction accuracy of the statistical model is increased for the provided training database. This is a form of machine learning. The statistical model is stored in a computer memory of the server.

Running of the computer readable program further comprises, or causes the server to execute the following steps.

Client data is received from a client application, the client data comprising time data and location data. The client data is provided as input to the statistical model to generate a recommended medication to a user of the client device, and a recommendation message is sent to the user, the recommendation message comprising the recommended medication.

According to further embodiment of the server preparation method, the statistical model comprises a decision tree and the adjusting of the statistical model comprises: starting from a root node, splitting the training database in two branches using a decision rule and thereby generating a new child node for each of these two branches, wherein the decision rule is chosen to maximize an information gain. For each new child node, the splitting is repeated until the training database cannot be split any further.

According to further embodiment of the server preparation method, the statistical model comprises a decision tree and wherein the adjusting of the statistical model comprises adjusting values of branching criteria of nodes of the decision tree based on the client data and on an outcome from the response message, wherein the outcome indicates whether the recommended medication was successful.

According to further embodiment of the server preparation method, the statistical model comprises a decision tree and adjusting of the statistical model comprises adding and/or removing branches to the decision tree based on the client data and on an outcome from the response message, wherein the outcome indicates whether the recommended medication was successful.

According to further embodiment of the server preparation method, the statistical model comprises a random forest and the adjusting of the statistical model comprises generating a random forest using the training database and measuring the statistical model accuracy on the test database.

According to further embodiment of the server preparation method, the statistical model comprises a gradient boosting trees model, the method comprises an adjusting of the statistical model, and the adjusting of the statistical model comprises the following steps.

Fitting a statistical model to the training database, computing a difference between a predicted output of the statistical model and a ground truth of the training database (33), wherein the ground truth can be provided by the outcomes of the migraine event data in the training database.

A new model is fitted to the computed difference, and an improved statistical model is obtained as a sum of the statistical model and the new model. The above steps are repeated until a predetermined prediction accuracy is reached.

According to further embodiment of the server preparation method, the statistical model comprises a gradient boosting trees model, the method comprises an adjusting of the statistical model, and the adjusting of the statistical model comprises the following steps.

Generating a sequence of decision trees by fitting a first decision tree to the training database, computing an output of the decision tree using the training database, computing a difference between the training database (33) and the output of the decision tree, deriving a loss function from the difference, and computing a gradient of the loss function.

A further decision tree is computed using the gradient of the loss function, an improved statistical model is obtained as a sum of the outputs of the previously computed first decision tree and the further decision tree. Until a predetermined accuracy of prediction is reached, the steps of computing a difference between the training database and the output of the decision tree, of deriving a loss function from the difference, of computing a gradient of the loss function, of computing a further decision tree using the gradient of the loss function, and of obtaining an improved statistical model as a sum of the outputs of the previously computed decision trees and the further decision tree are repeated.

In a further aspect, which is related to the server preparation method, the specification discloses a server that is preparable for providing a migraine medical drug recommendation or suggestion message. The server comprises a database on the or connected to the server. The database comprising user data sets, and each user data set comprises a migraine event or migraine event data, an applied recommendation, and an outcome.

Furthermore, the preparable server comprises a computer readable memory with a computer readable program. The computer readable program comprises a statistical model=and a statistical model adjuster. The computer readable program is operative to partition the database into a training data base and a test data base, for example by determining data set sizes and random sampling of user data sets with or without replacement.

Furthermore, the computer readable program is operative to provide the training database as input data to the statistical model adjuster, to build a statistical model based on the training database, to provide the test database as input to the statistical model, and to evaluate the statistical model based on the test database, The evaluating can comprise comparing predicted outcomes for recommended medication for data sets in the test database with predicted outcome and recommended medications in the training database.

The steps for adjusting the model may be repeated if a difference between the predicted outcomes is above a threshold.

According to a further embodiment of the preparable server, the statistical model comprises a decision tree and the adjusting of the statistical model comprises:

Starting from a root node, splitting the training database in two branches using a decision rule and thereby generating a new child node for each of these two branches, wherein the decision rule is chosen to maximize an information gain, and for each new child node, repeating the splitting until the training database cannot be split any further.

According to a further embodiment of the preparable server, the statistical model comprises a decision tree and the adjusting of the statistical model comprises adjusting values of branching criteria of nodes of the decision tree based on the client data and on an outcome from the response message, wherein the outcome indicates whether the recommended medication was successful.

According to a further embodiment of the preparable server, the statistical model comprises a decision tree and the adjusting of the statistical model comprises adding and/or removing branches to the decision tree based on the client data and on an outcome from the response message, wherein the outcome indicating whether the recommended medication was successful.

According to a further embodiment of the preparable server, the statistical model comprises a random forest and the adjusting of the statistical model comprises generating a random forest using the training database and measuring the statistical model accuracy on the test database.

According to a further embodiment of the preparable server, the statistical model comprises a gradient boosting trees mode, the method comprises an adjusting of the statistical model, and the adjusting of the statistical model comprises:

Fitting a statistical model to the training database, computing a difference between a predicted output of the statistical model and a ground truth of the training database ground truth. A new model is fitted to the computed difference, and an improved statistical model is obtained as a sum of the statistical model and the new model.

Until a predetermined prediction accuracy is reached, the steps of computing a difference between a predicted output of the statistical model and the training database, of fitting a new model to the computed difference, of obtaining an improved statistical model as a sum of the previously computed statistical model and the new model, are repeated.

According to a further embodiment of the preparable server, the statistical model comprises a gradient boosting trees model, the method comprises an adjusting of the statistical model, and the adjusting of the statistical model comprises generating a sequence of decision trees by the following steps:

Fitting a first decision tree to the training database, computing an output of the decision tree using the training database, computing a difference between the training database and the output of the decision tree, deriving a loss function from the difference, computing a gradient of the loss function, computing a further decision tree using the gradient of the loss function, obtaining an improved statistical model as a sum of the outputs of the previously computed first decision tree and the further decision tree, The above steps are repeated until a pre-determined accuracy of prediction is reached.

In a further aspect, the specification discloses a client device for providing a migraine medical drug recommendation, the client device comprising a computer readable program (6) on a computer readable memory of the server. The computer readable program is operative to send client data from a client application to a server, the client data comprising time data and location data, the location data indicating a position of a client device of a user, the time data indicating an onset of a migraine event of the user This causes the weather data server to retrieve weather data that corresponds to the timestamp data and the location data. A recommendation message for a user of the client device is received by the client device. The recommendation message comprises the recommended medication, and the recommended medication is based on the client data and atmospheric pressure data that corresponds to the time data and the location data using a statistical model.

A request message is received at the client device, the request message containing a first question whether the user took a medication according to the recommendation message, and a second question whether the medication was successful. The computer readable program further sends a response message to the request message to the server.

In comparison to traditional approaches, whereby the process of patients acquiring medications include obtaining prescription medications by visiting a doctor and purchasing over-the-counter (OTC) drugs recommended by a general website or by people around, a medication recommender according to the present specification can provide a time-saving and cheaper solution to identify and obtain a suitable medication.

Furthermore, the medication recommendation system can provide additional benefits to both doctors and patients. Among others, the medication recommendation system can receive more relevant data input than is provided in a typical short consulting session with a doctor. Thereby, the medication recommendation system can obtain an improved understanding of the relevant aspects of a patient's disease.

The medication recommendation system provides a means for obtaining sufficiently accurate information of patients, despite the complexity of the human brain and the varying quality of the data provided by users, which can be caused by lack of domain knowledge and various other behavioural and social effects, among others.

The recommendation system provides a ranked list of the best suitable drugs for migraine patients, but it can also be used for other diseases. The recommender system can provide a selection of a drug based on a combination of factors including the lifestyle, state, and previous reaction to other drugs of the patient. Specifically, the recommendation can be adjusted "per attack" for more complex patients, and it can be adjusted if the patient is following a program improving his/her lifestyle, such as a diet adjustment which reduces sensitivity to certain attacks.

The drug recommendation may be used by private users, but also by hospitals, for example for proving outcome improvement associated to their services, by insurers, for example for providing recommendations, by pharma professionals, for example for obtaining a higher improvement associated to their drugs. The medication recommender can provide an improved quality of recommendation, thanks to the amount of data collected by different users worldwide for continuously training the algorithm.

Three important aspects of a medication recommender according to the current specification, which contribute to a reliable recommendation system, are:
1) spell-checking of free-text input by users
2) categorization of medical terms (including, but not limited to, triggers, symptoms, and medications)
3) predicting the effect of drug molecules Among others, the medication recommender can be used to help patients and assist a specialist in several scenarios:
1. In case a specialist needs to prescribe new drugs for the patient, a personalized ranked list provided by the medication recommender can limit the number of drug choices available, avoid unnecessary drug side effects and contribute to overall patient satisfaction. The recommendation system can provide a suitable selection of medications from several available medications to provide a timely and effective remedy for the migraine.
2. If the patient already has several available drugs, the medication recommender can recommend the most likely effective drug through a ranked list provided by the medication recommender. For example, a list can be provided by the following procedure: The last N migraines of the user, where N is a suitably chosen number, are used to make predictions on the outcomes. Then a weighted average is calculated to determine whether this medication is useful for his future migraines. In such a case, the model will treat it as a classification problem, and it is able to generate the outcome as helpful or unhelpful.
3. If the patient doesn't have any drug names in mind, the medication recommender can suggest the usage of one suitable likely helpful drug for him. For example, the recommendation system can predict the probabilities of helpfulness of a list of medications and produce a ranked list.

Among others, the medication recommender can implement the following methods listed below.

1. Content-Based Filtering

A content-based filtering method is based on the preferences of a user and the features of items and requires the users to actively interact with the recommender system so that the system can recommend items similar to those with positive feedbacks from the users. Due to delayed effects of medications and potential lack of interaction between users and the recommender system, a content-based filtering method is less suitable for a recommender system according to the present specification, although it may be used.

2. Collaborative Filtering

Collaborative filtering methods make recommendations to a user based on feedback from similar users, which follows the rationale that if an active user shares similar attributes with some other users in the past, this user will have a higher likelihood of also having commonalities with other users in the future. By taking advantage of the large amount of information of similar users, this approach does not require the feedback of similar items from the user in the past to make recommendations.

3. Hybrid Recommender Systems

As the term implies, this type of recommender systems employs combinations of multiple techniques to gain advantages over a single approach. For example, the recommender system can implement a combination of random forest, XGBoost and sequential neural network methods to arrive at a recommended medication.

In particular, the current specification disclose a medication recommendation system for the prediction and the ranking or rating of medications for migraine based on self-reported data. In particular, the recommendation system can provide a recommended medication and dosage regime of the recommended medication, a recommended nutrition or a nutrition to avoid, a recommended activity or an activity to avoid and other measure that may have positive influence on a migraine event or can help to avoid the migraine event altogether.

The recommendation system comprises a server device with server database. Wherein the server device can be provided by a dedicated computing device or by cloud based resources, among others.

Furthermore, the recommendation system comprises a client computer device, which can be in particular a mobile computer device such as a laptop, a mobile phone, a touchpad, a wearable computer device or any other type of mobile computer device or also a personal computer such as a desktop computer. In summary, the client computer device can be a mobile computer device or a wearable computer device or any non-mobile computing device or alike.

The client computer device comprises an environment sensor for measuring an environment variable, such as a pressure, electromagnetic field, such as a light intensity or a magnetic field strength, or an acceleration or other movement of the client device.

The evaluation of data from the environment data can help to improve a recommendation of the recommendation system. For example, in one embodiment an environmental pressure used in a data evaluation or processing as a contributing factor of a migraine event. In other embodiments, the recommendation system of the present specification is realized without evaluation of data from an environment sensor.

The client device comprises a computer memory with a recommendation application or computer program and with a client database, and with a communication means, such as a transmitter for communicating with the server device over a communication link, which may in particular comprise a wireless communication link.

The recommendation application is operative to receive self-reported data of a user of the client computer device over a user interface of the recommendation application, to receive environment data from the environment sensor, and to retrieve user-specific data from the client database, such as the intensity and the duration of a migraine event, a medication type and dose taken before the event, a drug or medication intake time, a pre-determined activity taking place in a pre-determined time interval, a user demographic data such as age, sex, BMI, profession, duration and time of sleep, complications and comorbidities or other migraine influence factors, whether or not they are contributing to or alleviating the migraine event, and a rating of their influence by the user.

Furthermore, the recommendation system generates a recommendation request message, the recommendation request message comprising the self-reported data, the environment data, and the retrieved user-specific data, and sends the recommendation request message over the communication link, using the communication means.

The server device is operative, by means of suitable software and/or hardware, to receive the recommendation request message, to retrieve recommendation related data from the server database, and to derive a recommendation within a pre-determined request response time. In particular the server device can predict and rank an outcome of a migraine medication.

The deriving of the recommendation comprises applying at least one statistical procedure to the input data to obtain recommendation output data, the input data comprising data of the recommendation request message and the recommendation related data, wherein the at least one statistical procedure comprises at least one of a random forest method, a gradient boost method and a sequential neural network method.

The server device is further operative to generate a recommendation response message, the recommendation response message comprising the recommendation output data, to send the recommendation response message to the client device over the communication link.

According to a further embodiment, the server device is operative to collect self-reported data from a multitude of other users from different countries, and to store the self-reported data in a central repository, such as the server database. In particular, the multitude of users can be distributed over different continents or even around the inhabited world. Specifically, the multitude of users can refer to a large number of users exceeding a hundred thousand users, a million users or even ten million users or more.

According to a further embodiment, the server device is operative to receive user data records, to process the user data records and to transmit model data to the mobile device, whereby a prediction accuracy of the medication recommendation can be enhanced. The model data is derived from the collected self-reported data of the multitude of other users.

According to a further embodiment, a mode of collection comprises active reporting through a form of the recommendation application and/or passive acquisition through a sensor of the at least one environment sensor.

According to a further embodiment, the client computer device is further operative to identify and display a recommended form of administration of a migraine medication, the form of administration being selected from enteral, parenteral and topical routes of administration.

According to a further embodiment, the client computer device is a mobile computer device and/or a wearable computer device, which enables to user to conveniently receive a recommendation where and when it is needed. The recommendation may be provided online or offline by using cached data from the server. A data exchange between the client device and the server device may be initiated when the client device detects a connection to the communication link and/or based on a schedule.

According to a further embodiment, the input data to the at least one statistical procedure comprises symptoms, triggers, demographics, environment, or previous drug outcome of the user, or a combination thereof.

According to a further embodiment, the client device is further operative to process the self-reported data and/or the user specific data of the client database, wherein the data processing comprising one or more of molecule matching, spell checking, and categorizing symptoms, triggers, medical terms and medications.

According to a further embodiment, the client computer device or the server device is operative to translate an input medication provided by a user of the mobile computer device into an active ingredient, through use of drug dictionary, previous self-reported data, a custom dictionary, or a combination thereof.

According to a further embodiment, the client computer device is operative, through use of a spell checker, to correct misspelled words of the self-reported data based on similarity and edit distance in relation to stored words in in a MB database, or drug database, or a combination thereof. The MB database or the drug database may be provided by the client database or also by the server database.

According to a further embodiment, the mobile device is operative to categorize symptoms, triggers and other medical terms by comparison with data in the client database and/or the server device.

According to a further embodiment, the machine learning models include stacking with XGBoost, Random Forest, sequential neural networks techniques, or a combination thereof.

According to a further embodiment, the server device is operative to synchronize user data between different devices, the synchronizing comprising determining a time overlap between user data relating to a first migraine event and a second migraine event and determining, based on the time overlap, whether the first migraine event and the second migraine event corresponds to the same migraine event, and, if it is determined that the first migraine event and the second migraine event correspond to the same migraine event, merging the data of the first migraine event with the data of the second migraine event.

In a further aspect, the present specification discloses a computer-implemented medication recommendation method for a rating of medications for migraine based on self-reported data, the recommendation system comprising a server device, which may be provided by a dedicated computing device or by cloud based resources, wherein the server device comprises a server database. Furthermore, the recommendation system comprises a client computer device with an environment sensor for measuring an environment variable, such as pressure, electromagnetic field or others, and with a recommendation application or computer program and a client database. The client device also comprises a communication means, such as a transmitter, for communicating with the server device over a communication link.

The client device receives self-reported data of a user of the client computer device over a user interface of the recommendation application, receives environment data from the environment sensor, retrieves user-specific data from the client database, and generates a recommendation request message. the recommendation request message comprises the self-reported data, the environment data, and the retrieved user-specific data. The client device sends the recommendation request message over the communication link, using the communication means.

The server device receives the recommendation request message, retrieves recommendation related data from the server database, and derives a recommendation, such as a medication recommendation, within a pre-determined request response time.

The deriving of the recommendation comprises applying at least one statistical procedure to the input data to obtain recommendation output data, the input data comprising data of the recommendation request message and the recommendation related data. Therein, the at least one statistical procedure comprising at least one of a random forest method, a gradient boost method and a sequential neural network method.

The server generates a recommendation response message, the recommendation response message comprising the recommendation output data, and sends the recommendation response message to the client device over the communication link.

According to a further embodiment, the method further comprises collecting self-reported data from a multitude of other users from different countries around the world, and/or from different continents around the world and to store the self-reported data in a central repository, such as the server database.

According to a further embodiment, the method further comprises receiving user data records, processing the user data records, retrieving model data from the server database and transmitting model data to the mobile device. Thereby, a prediction accuracy of the medication recommendation is enhanced, wherein the enhancement refers to an average improvement of the prediction across the users connected to the server device but may not apply in every single case. The model data is derived from the collected self-reported data of the multitude of other users.

According to a further embodiment of the method, a data collection comprises active reporting through a form of the recommendation application and/or passive acquisition through a sensor of the at least one environment sensor.

According to a further embodiment, the method further comprises identifying and displaying a recommended form of administration of a migraine medication, the form of administration being selected from enteral, parenteral and topical routes of administration.

According to a further embodiment of the method, the client computer device is provided by a mobile computer device or a wearable computer device.

According to a further embodiment of the method, the input data to the at least one statistical procedure comprises symptoms, triggers, demographics, environment, or previous drug outcome of the user, or a combination thereof.

According to a further embodiment, the method further comprising processing the self-reported data and/or the user specific data of the client database, wherein the data processing comprising one or more of molecule matching, spell checking, and categorizing symptoms, triggers, medical terms and medications.

According to a further embodiment of the method, the client computer device or the server device is operative to translate an input medication provided by a user of the mobile computer device into an active ingredient, through use of drug dictionary, previous self-reported data, a custom dictionary, or a combination thereof.

According to a further embodiment, the method further comprises correcting, through use of a spell checker, misspelled words of the self-reported data based on similarity and/or edit distance in relation to stored words in the client database.

According to a further embodiment, of the method, the mobile device is operative to categorize symptoms, triggers and other medical terms by comparison with data in the client database and/or the server device.

According to a further embodiment of the method, the machine learning models include stacking with XGBoost, Random Forest, sequential neural networks techniques, or a combination thereof.

According to a further embodiment, the method further comprises synchronizing user data between different devices, the synchronizing comprising determining a time overlap between user data relating to a first migraine event and a second migraine event and determining, based on the time overlap, whether the first migraine event and the second migraine event corresponds to the same migraine event, and, if it is determined that the first migraine event and the second migraine event correspond to the same migraine event, merging the data of the first migraine event with the data of the second migraine event.

In a further aspect, the present specification discloses a recommendation system for a rating of medications for migraine based on self-reported data, which is also referred to as "user data". The recommendation system comprises a mobile device or a terminal unit, such as a mobile phone, a laptop, a personal computer or the like. The mobile device can also be provided by a wearable electronic such as a smart watch, which is able to communicate over a wireless network.

The mobile device is operative to communicate with a server over a communication link. Among others, the mobile device is operative to send the self-reported data to the server, to receive from the server a drug recommendation that is based on the self-reported data, and to receive information from the server about suitable drugs, treatments and recommend actions to take, wherein the information may be based on the self-reported data or it may be general information.

The mobile device is operative to receive self-reported data of a user over a user interface and to send the self-reported data to the server. For example, the user interface can be provided by a graphical user interface, which provides input fields for textual input, graphical elements for selecting items from lists of items, input buttons, sliders, turning knobs and the like.

Furthermore, the mobile device or the server is operative to predict and rank an outcome of a migraine medication based on the self-reported data and on the output data of at least one statistical procedure, such as a random forest method, a gradient boost method and a sequential neural network method, or a combination thereof. Preferentially, the prediction is carried out before the ranking and based on the ranking. In particular, the results of different statistical procedures can be combined to achieve an improved accuracy. Furthermore, the mobile device and/or the server is operative to derive a recommended migraine medication from the predicted outcome of the migraine medication or from multiple predicted outcomes of migraine medications which are compared to each other.

The recommendation can be provided, among others in terms of the choice of the medication and dosage, such as amount or time and choice of administration of the medication. Further recommendations can also be provided based on an evaluation of the user input data, for example a recommended course of action to avoid migraine attacks.

By using the medication recommendation system according to the present specification, a recommendation to a user of the mobile device can be provided in a timely and accurate manner and tailored to the individual requirements of a patient and without the need of a personal consultation. In particular in the case where the ranking and predicting is carried out on the server, the ranking and prediction can be improved by adjusting the ranking and prediction based on user input data provided by other users of the medication recommendation system while at the same time maintaining confidentiality of the input data.

By using a medication recommendation system according to the current specification, a large amount of user data can be taken into amount for providing the medication recommendation for the user of the mobile device within the short request period needed for sending the data to the server, carrying out the calculations on the server and sending the results back to the mobile device, which would not be practicable by calculating the time-consuming steps for providing the medication recommendation by hand.

In an embodiment in which the medication recommendation is derived on the mobile device itself, the calculation can also be improved based on input data of other users and calculations carried out for the other users by sending updated model parameters or calculation parameters from the mobile device to the server.

In order to provide confidentiality, the data traffic between the mobile device and the server can be encrypted by using a symmetric encryption, such as a public key encryption, asymmetric encryption or another encryption method.

Furthermore, the mobile device is operative to output the recommended migraine medication to the user of the mobile device over a user interface of the mobile device.

In a further embodiment, the mobile device is further operative to identify and display a recommended form of administration of a migraine medication. The form of administration is selected from enteral, parenteral and topical routes of administration. The mobile device may receive the recommended form of medication in a message from the server or derived by internal processing of the mobile device taking into account the input data provided by the user of the mobile device.

According to a further embodiment, the recommendation system comprises the server, and the server is operative to collect self-reported data from around the world and store the self-reported data in a central repository database.

According to a further embodiment, a mode of collection can be either active reporting through a form or passive acquisition through a sensor.

According to a further embodiment, sensor is provided by the mobile device or a wearable device, for example a smart watch such as Iwatch® or Fitbit®. For example, a sensor integrated in a mobile device can be used to provide measurements from a surface of the human body, such as body temperature, heart rate and so forth, and it can provide measurements of the environment like atmospheric pressure and other electromagnetic measurements.

According to yet a further embodiment, input parameters to the at least one statistical procedure include combinations of symptoms, triggers, demographics, environment parameters, previous drug outcome. Thereby, the medication recommendation can be tailored to the specific conditions of the mobile device user. By considering the above-mentioned factors, the medication recommendation can be improved and a comparison with medication recommendations provided for other users can be facilitated.

According to a further embodiment, a data processing of input data includes molecule matching, spell checking and categorizing symptoms, triggers, medical terms and medications. Thereby, the input of the data is facilitated and errors due to a faulty user input can be avoided, among others. Furthermore, an intelligent user input can be provided, which automatically suggests input data to the user based on previous user input or on other information stored on the mobile device.

According to a further embodiment, the mobile device or the server is operative to translate an input medication provided by a user of the mobile device into an active ingredient, through use of drug dictionary, previous input data, and custom dictionary.

According to a specific embodiment, the mobile device is operative, through use of a spell checker, to correct misspelled words based on similarity and edit distance.

According to a further embodiment, the mobile device or the server is operative to categorize symptoms, triggers and other medical terms. Thereby, a user input can be facilitated and an output to the user can be provided in a user-friendly manner. Furthermore, the deriving of the medication recommendation can be improved using the categorization.

According to a further embodiment, wherein the machine learning or statistical models include stacking with XGBoost, Random Forest, and sequential neural networks techniques.

According to a further embodiment, the server is operative to receive user data records, to process the user data records and to transmit model data to the mobile device, such that a prediction accuracy of the medication recommendation is enhanced.

In a further aspect, the present specification provides a method of providing a medication recommendation. According to this method, self-reported data of a user is received over a user interface, an outcome of a migraine medication is predicted and ranked based on the self-reported data and on the output data of at least one statistical procedure. The at least one statistical or machine learning procedure comprises at least one of a random forest method, a gradient boost method and a sequential neural network method.

According to a further embodiment, the method further comprises identifying a recommended form of administration of a migraine medication, which is selected from enteral, parenteral and topical routes of administration. The recommended form of administration is displayed on a user interface of the mobile device, such as a display screen or similar.

According to a further embodiment of the method, the method is executed on a recommendation system that further comprises the server, wherein the server is operative to collect self-reported data from around the world and store the self-reported data in a central repository database.

According to a further embodiment, the method comprises receiving user input through an input form of a graphical user interface. In a further embodiment, the method further comprises receiving user data via a sensor of a mobile device or a wearable device, wherein the user data may include, by way of example, blood pressure, body temperature, time of day, atmospheric pressure, or steps walked per day or other body or environment related parameters.

According to a further embodiment, input parameters to the at least one statistical procedure include combinations of symptoms, triggers, demographics, environment parameters, and previous drug outcome.

According to a further embodiment, the method comprises processing the input data, the processing of the input data comprising molecule matching, spell checking, categorizing of symptoms, triggers, medical terms and medications or a combination thereof. In a specific embodiment, the method comprises correcting misspelled words based on similarity and edit distance.

According to a further embodiment, the method further comprises translating an input medication provided by a user of the mobile device into an active ingredient, through use of a drug dictionary, of previous input data, and of a custom dictionary. According to yet a further embodiment, the method comprises categorizing symptoms, triggers and other medical terms.

According to a further embodiment, the machine learning models used in the method for deriving the medication recommendation include stacking with XGBoost, Random Forest, and sequential neural networks techniques.

According to a further embodiment, the method further comprises receiving user data records, processing the user data records and to transmit model data to a mobile device, such that a prediction accuracy of the medication recommendation is enhanced.

According to a further embodiment, the method comprises synchronizing user data between different devices, the synchronization comprising determining a time overlap between user data relating to a first migraine event and a second migraine event and determining, based on the time overlap, whether the first migraine event is different from the second migraine event.

Thereby, redundant data entry can be detected and avoided or eliminated and data corresponding to the same migraine event can be merged. Especially when a user provided input over different mobile devices is redundant or multiple data entry can occur, which can be rectified by using the above-mentioned method features.

Figure 2:
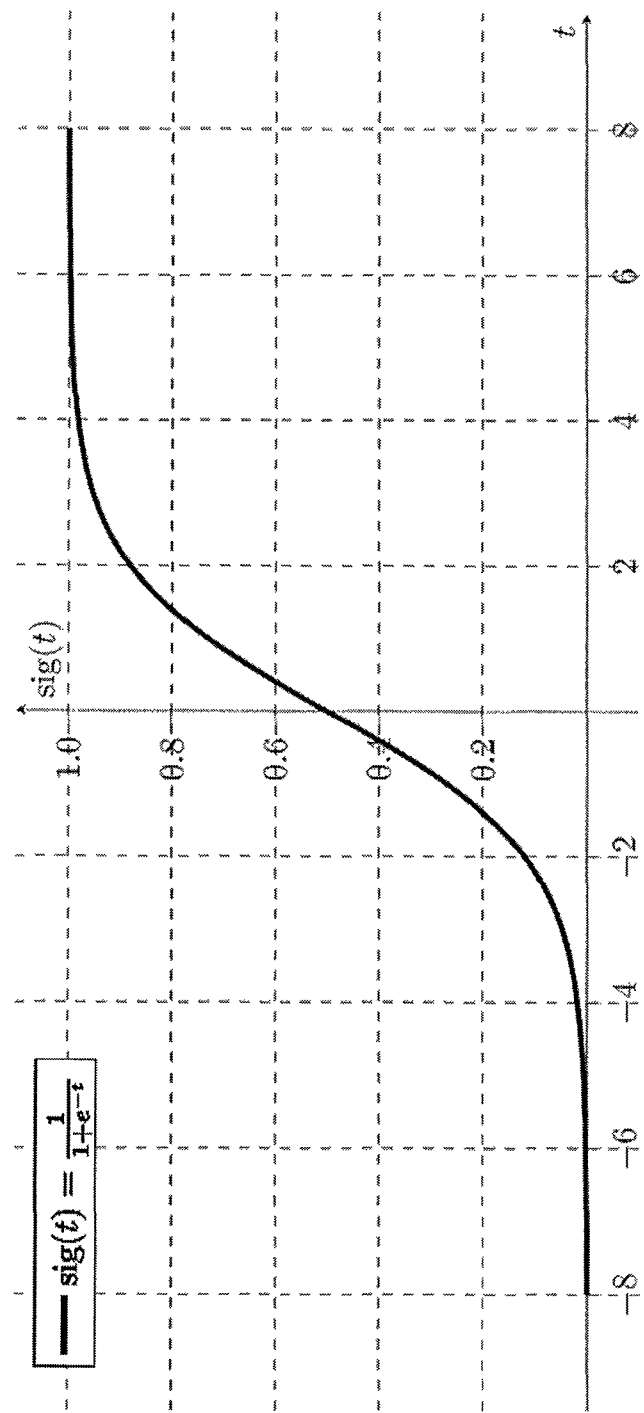
Figure 3:
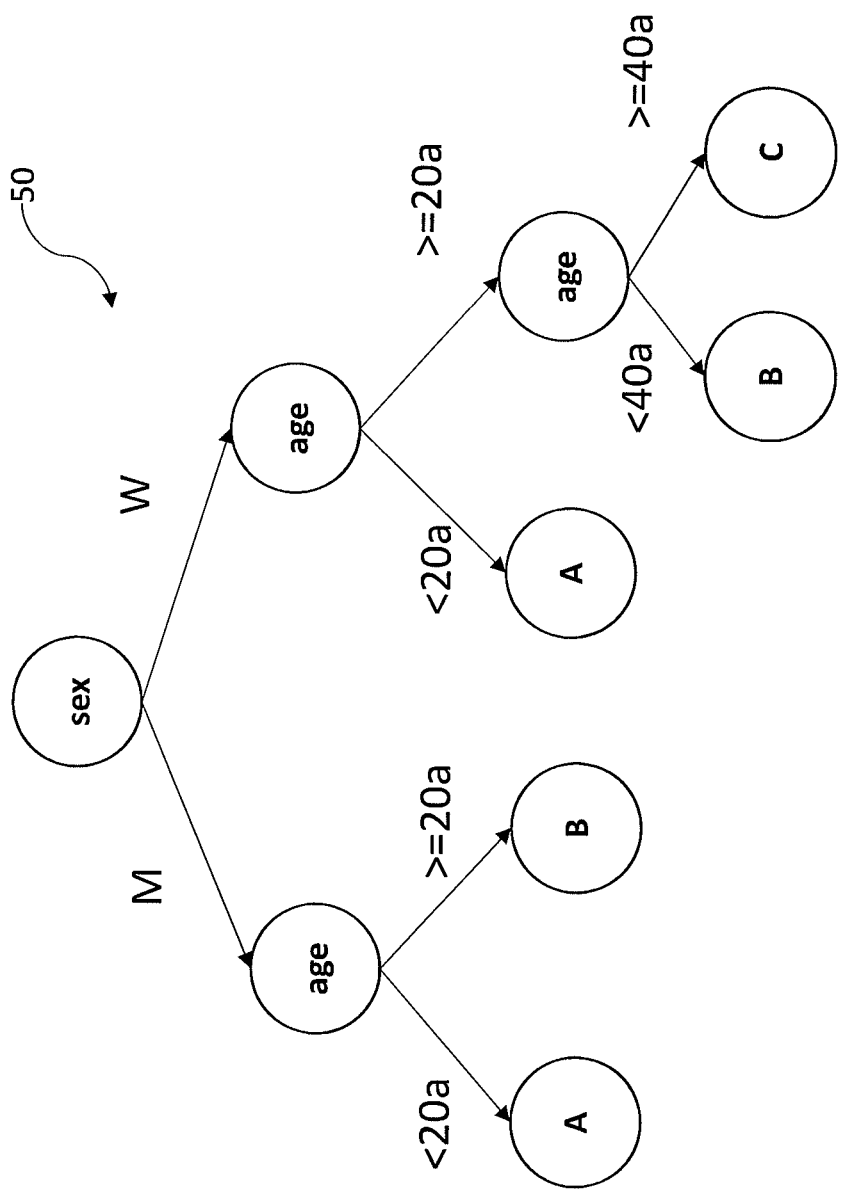
Figure 4:
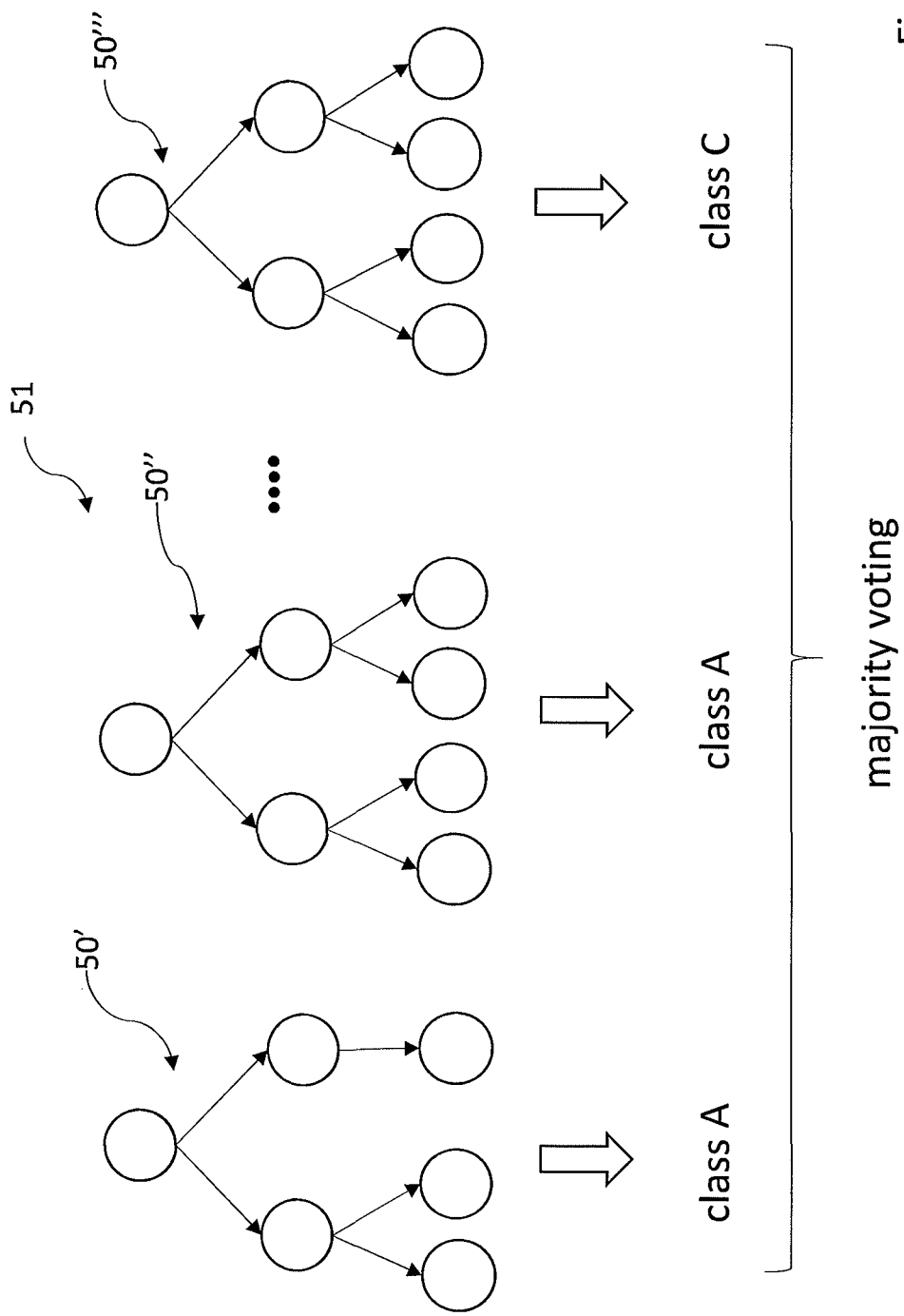
Figure 5:
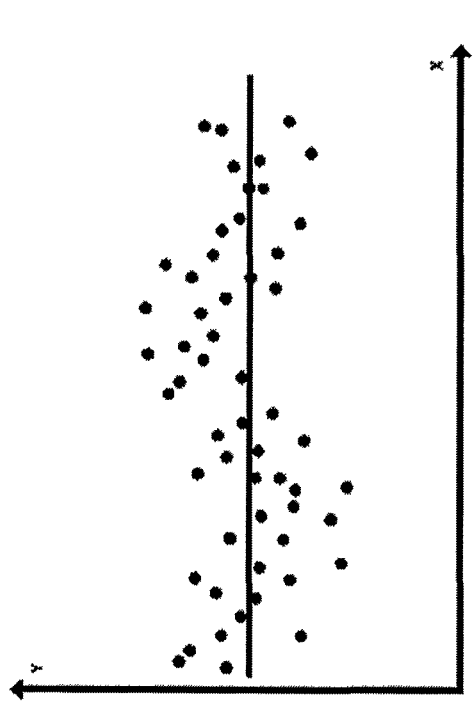
Figure 6:
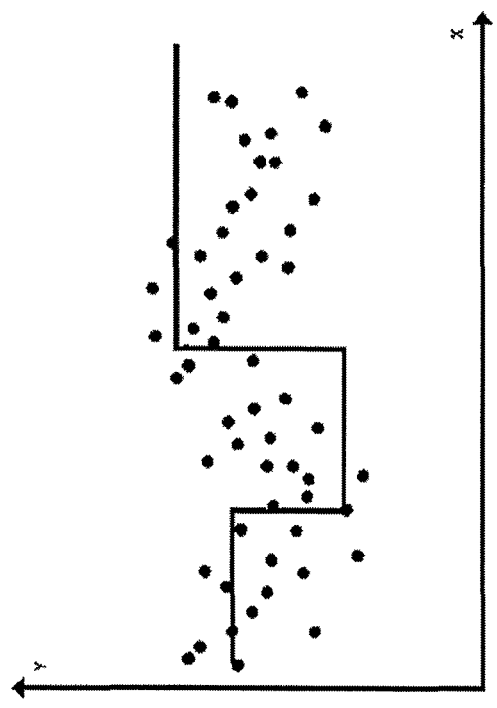
Figure 7:
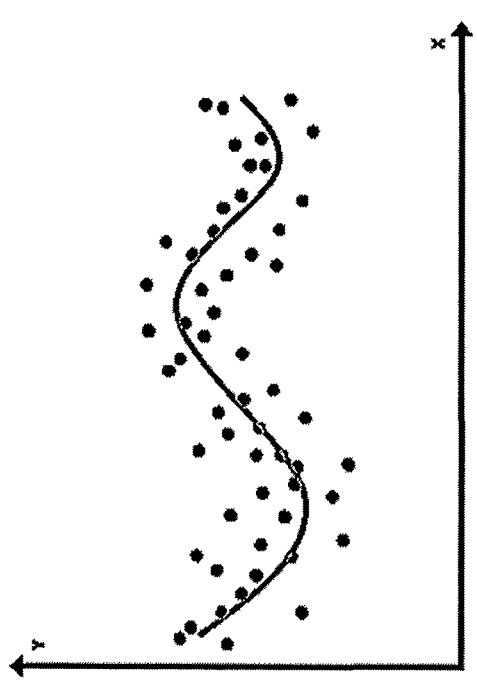
Figure 8:
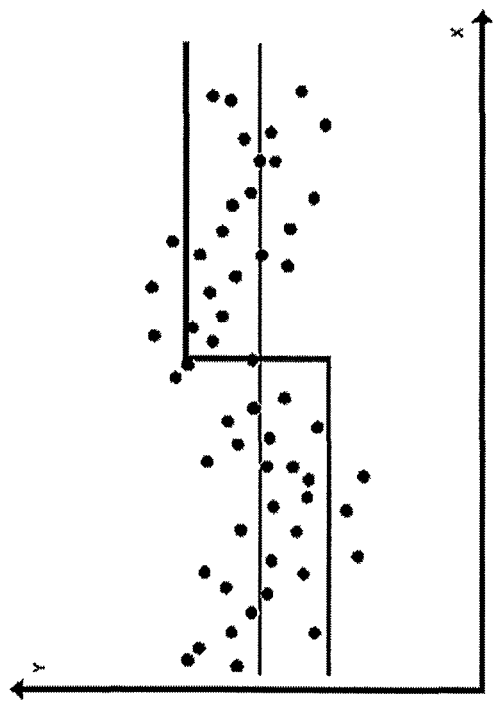
Figure 9:
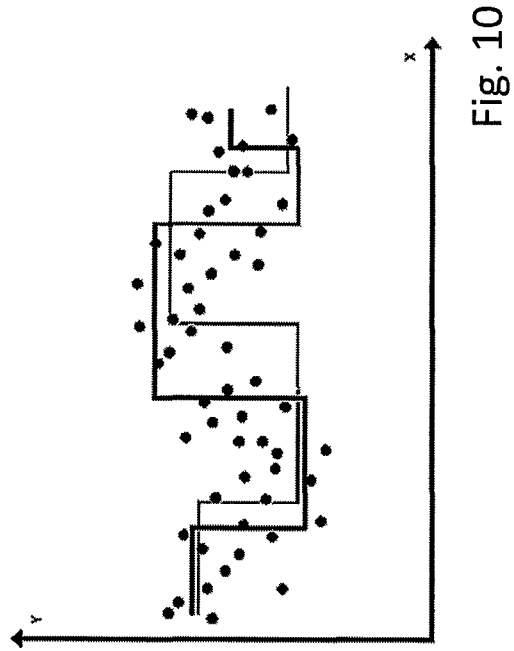
Figure 10:
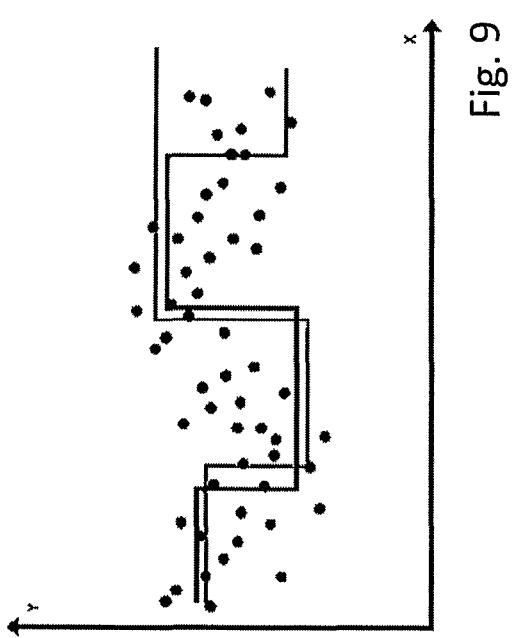
Figure 11:
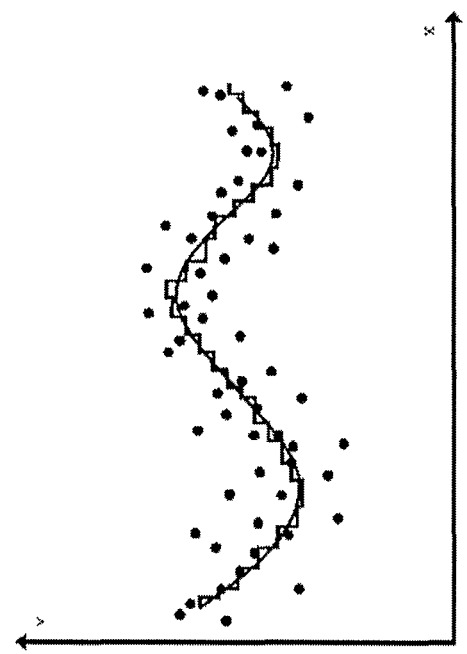
Figure 12:
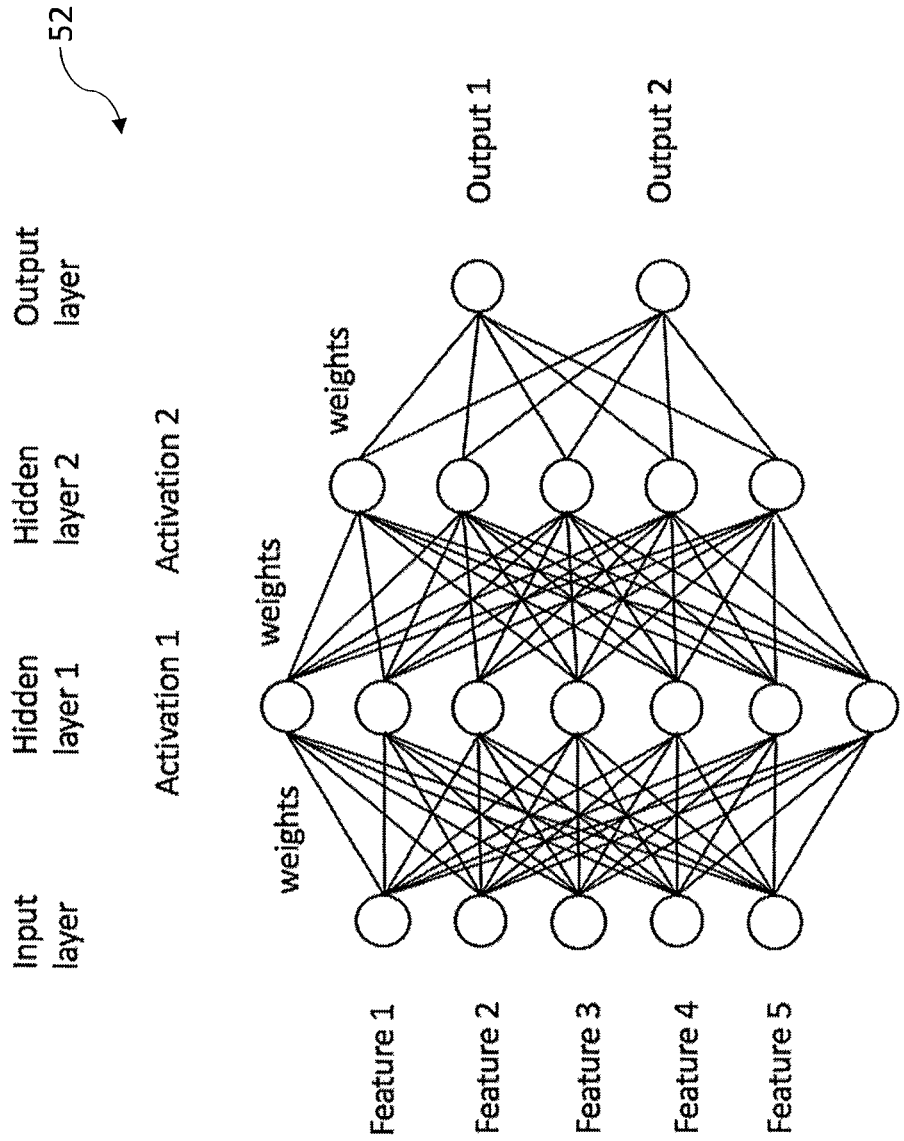
Figure 13:
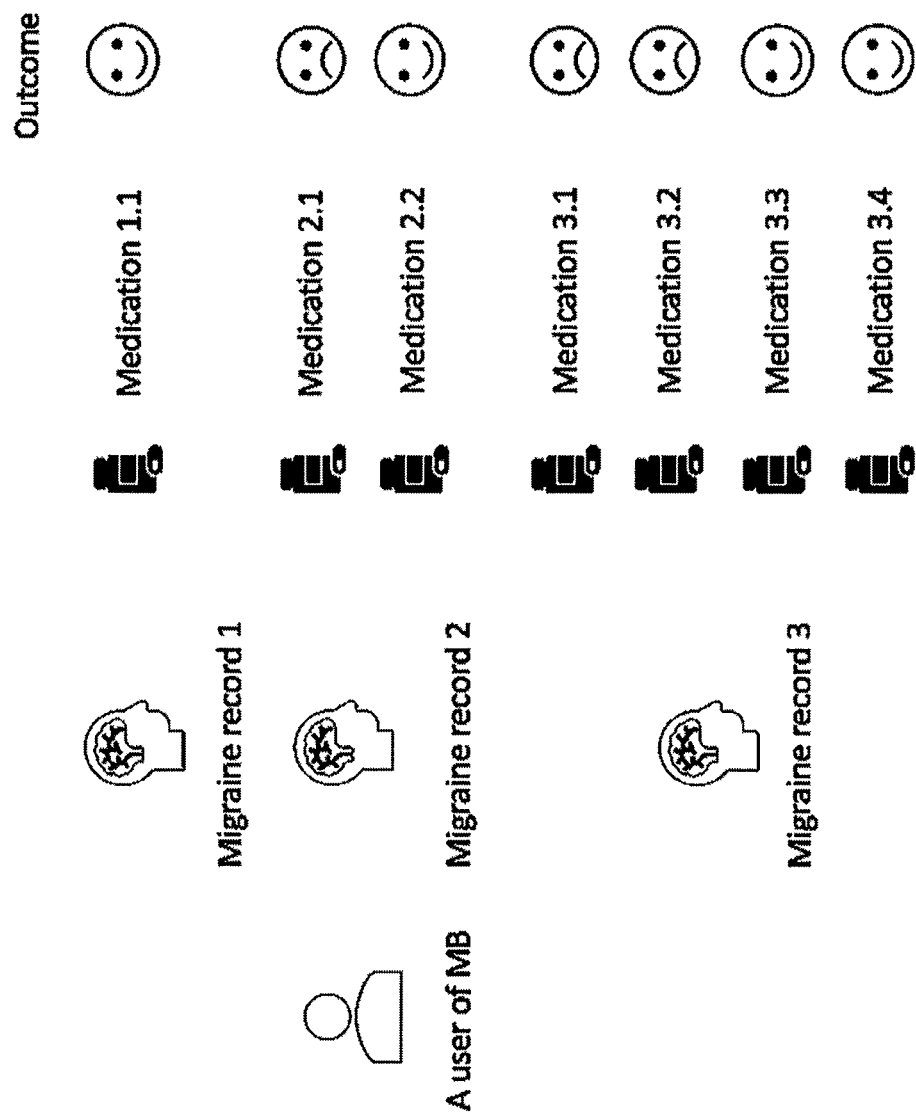
Figure 14:
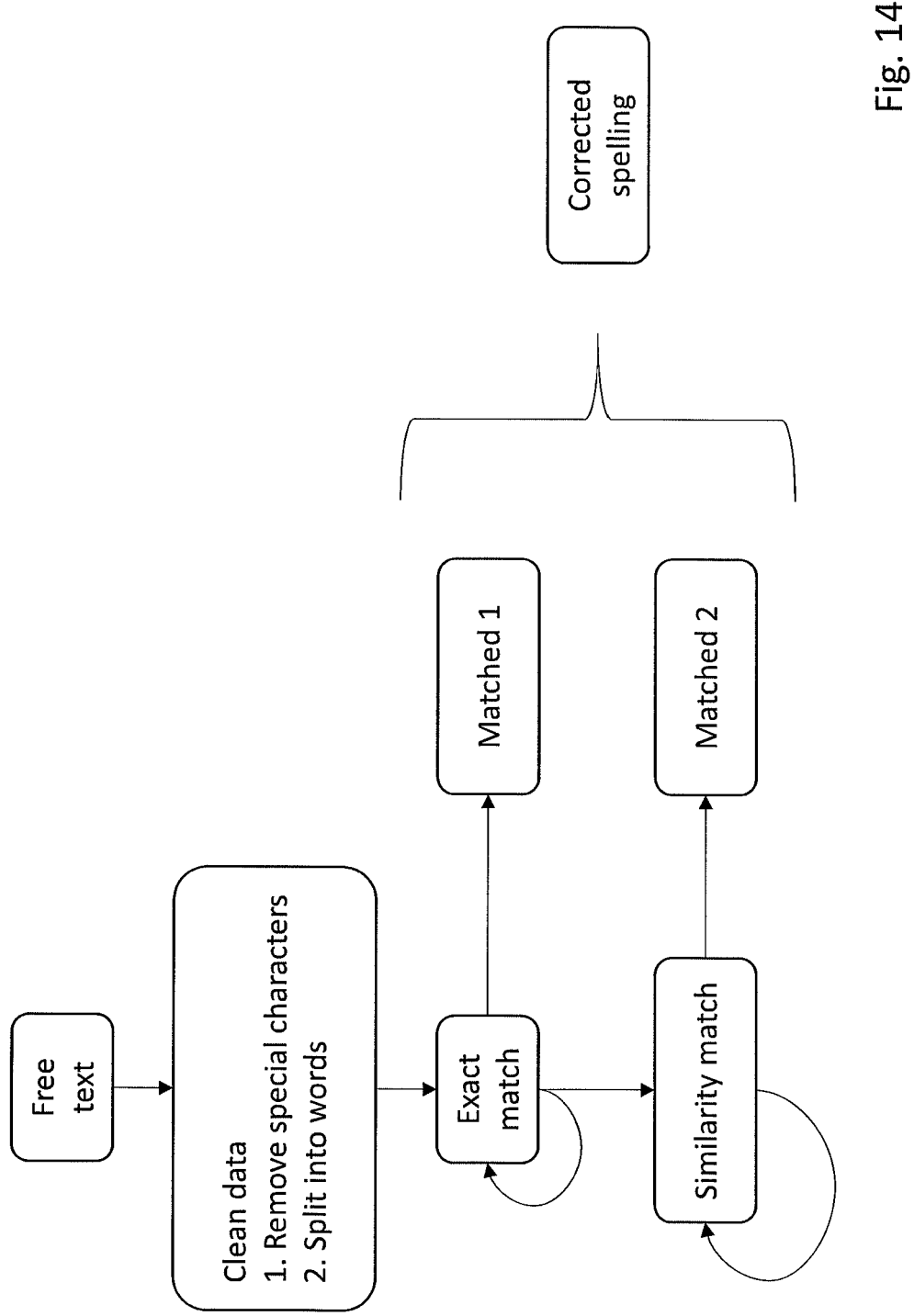
Figure 15:
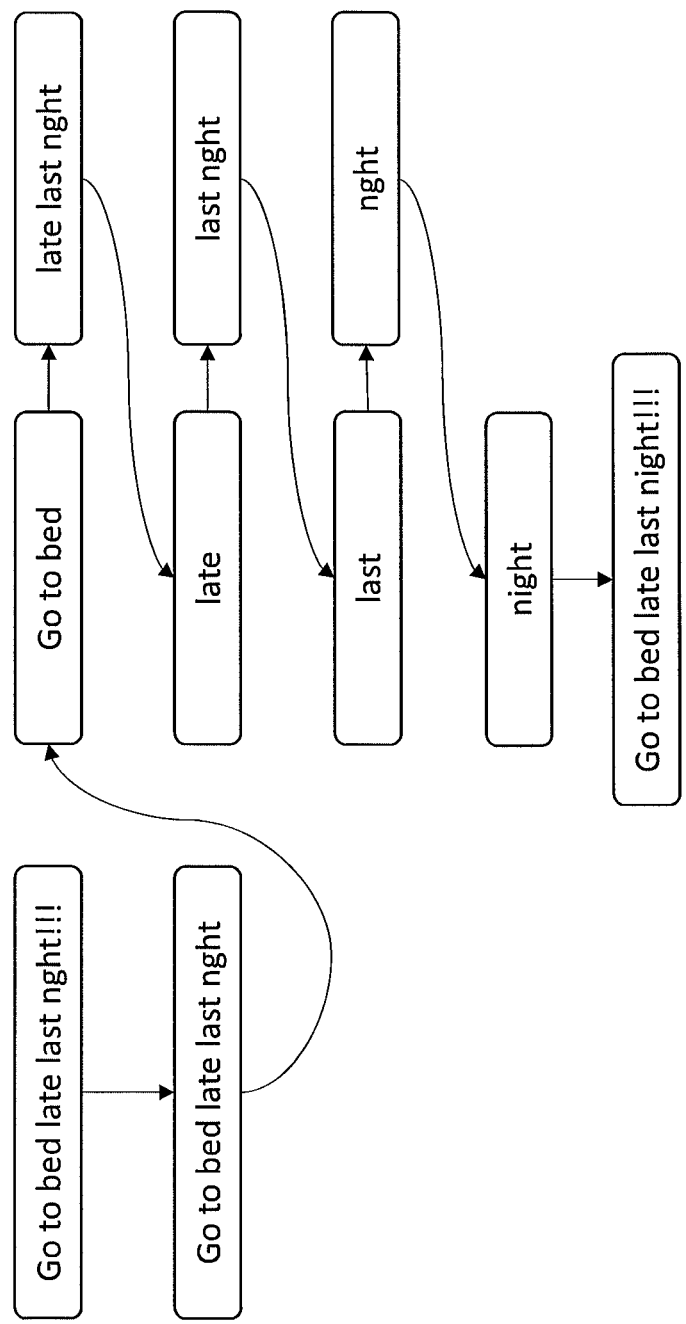
Figure 18:
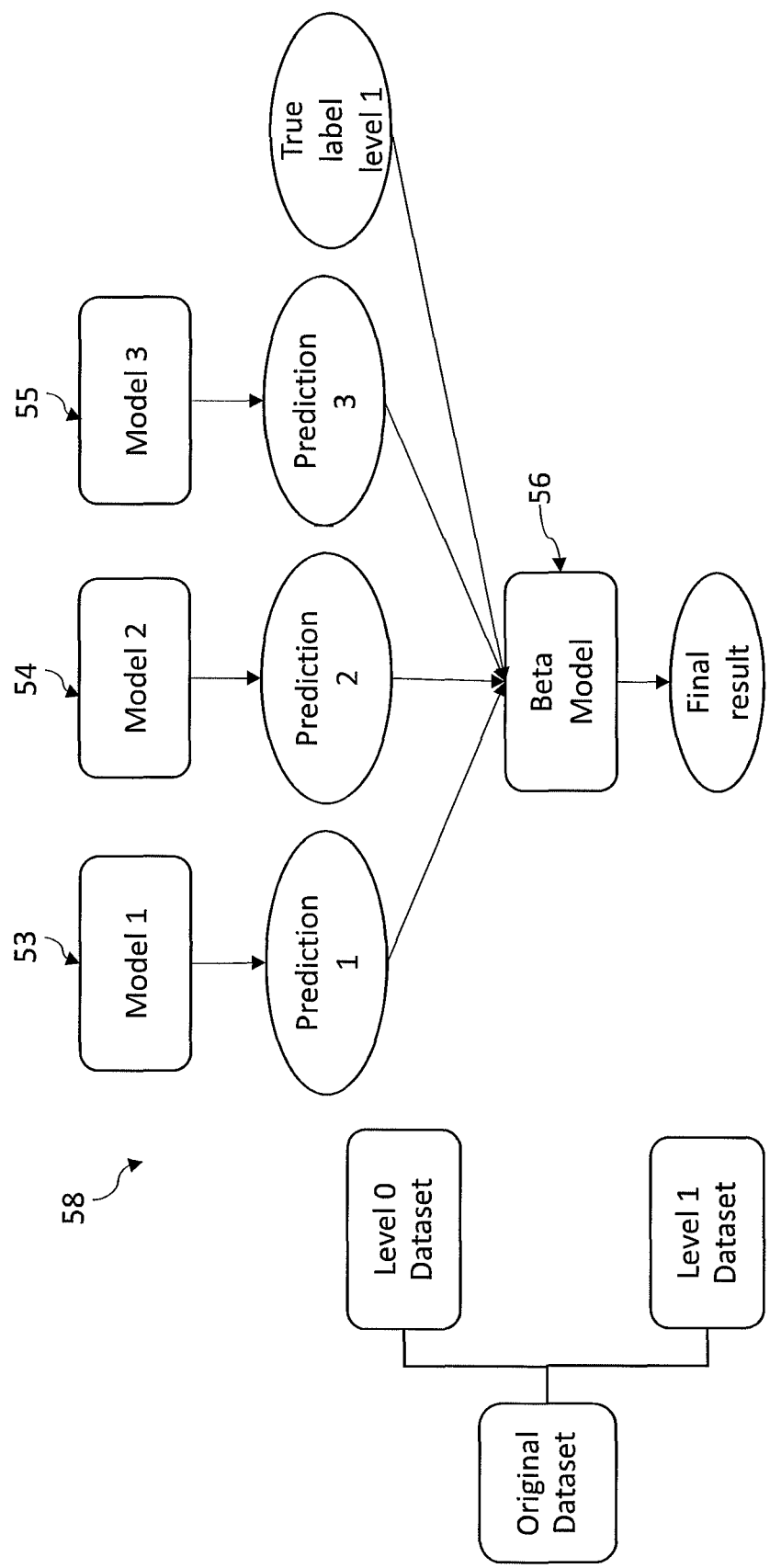
Figure 19:
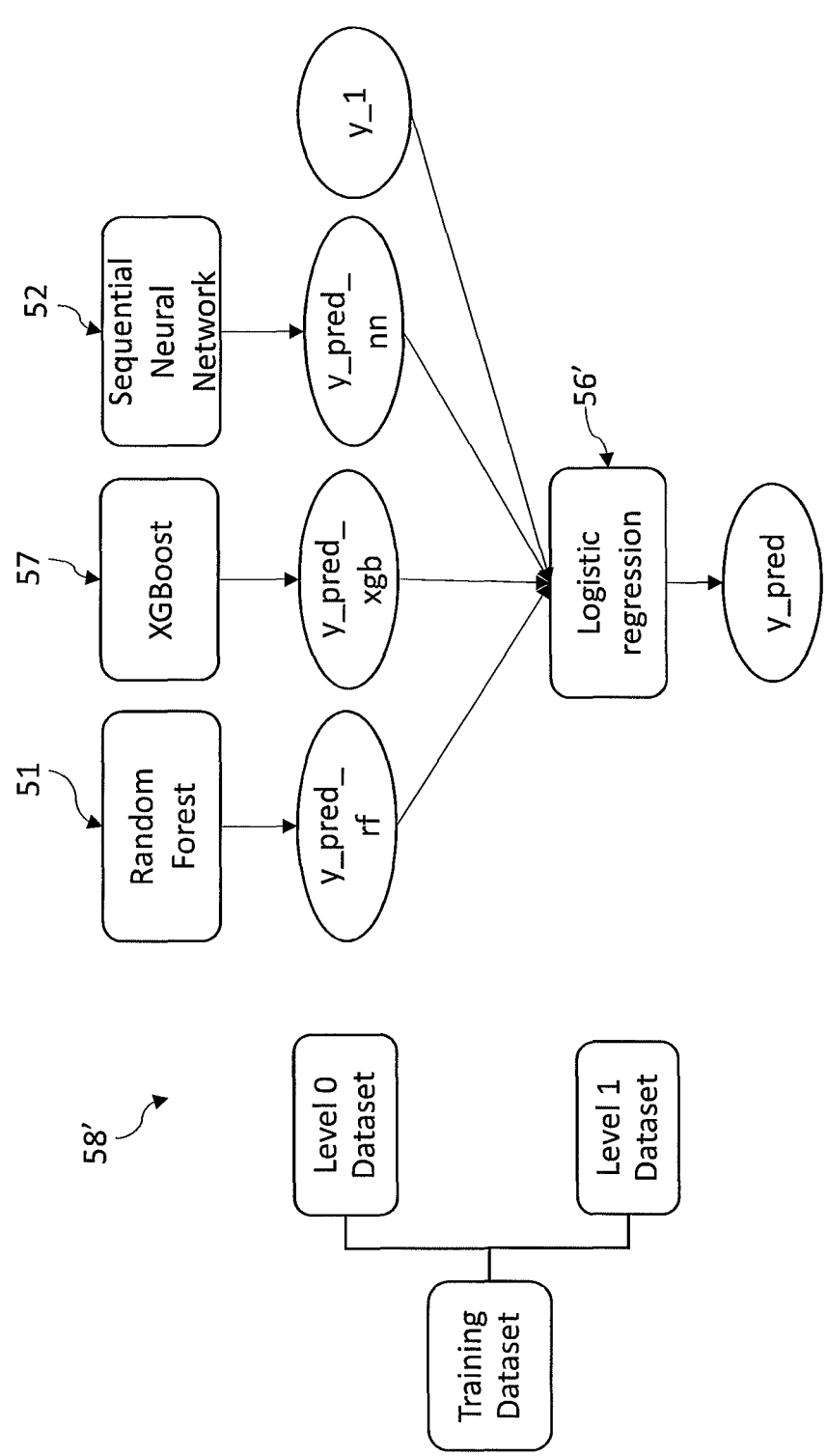
Figure 20:
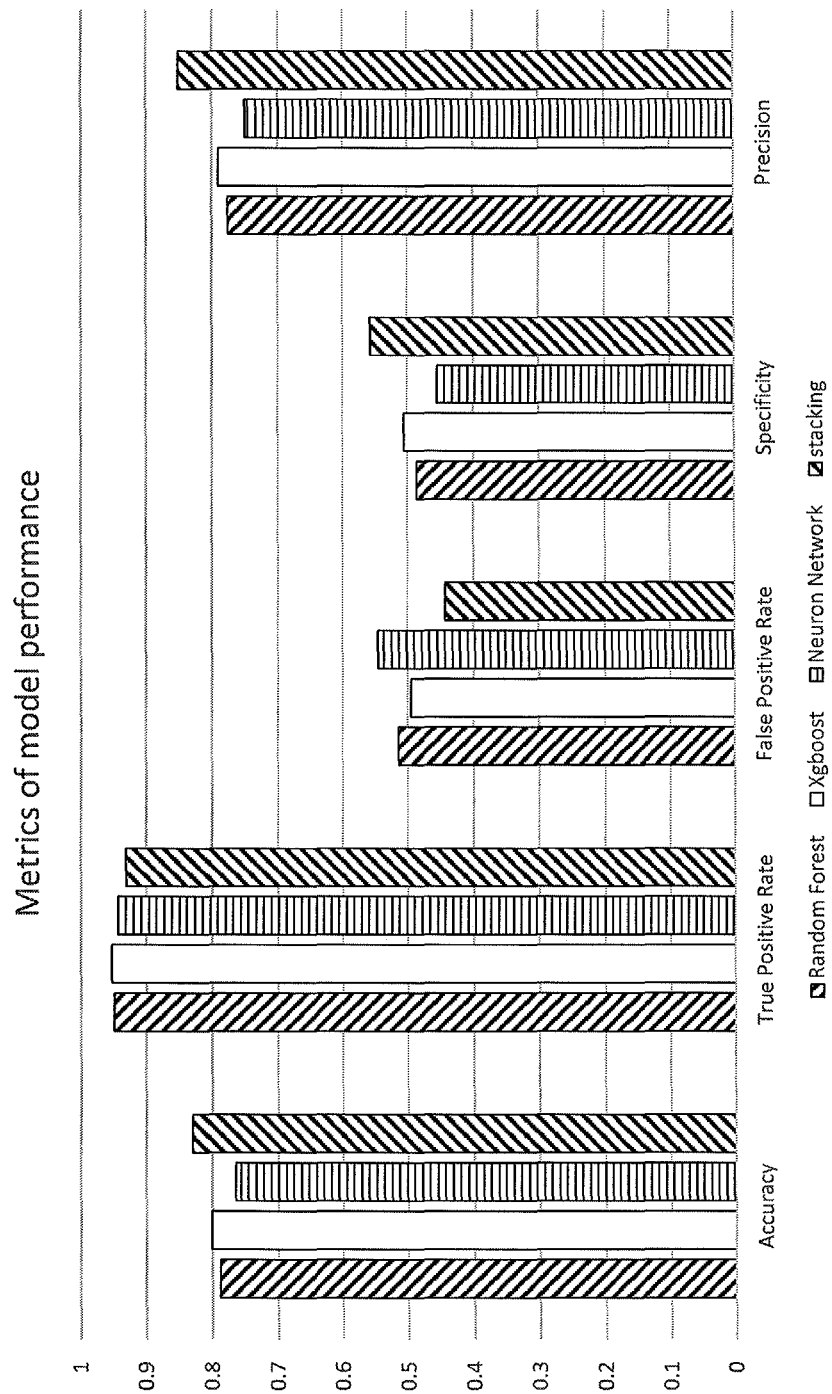
Figure 21:
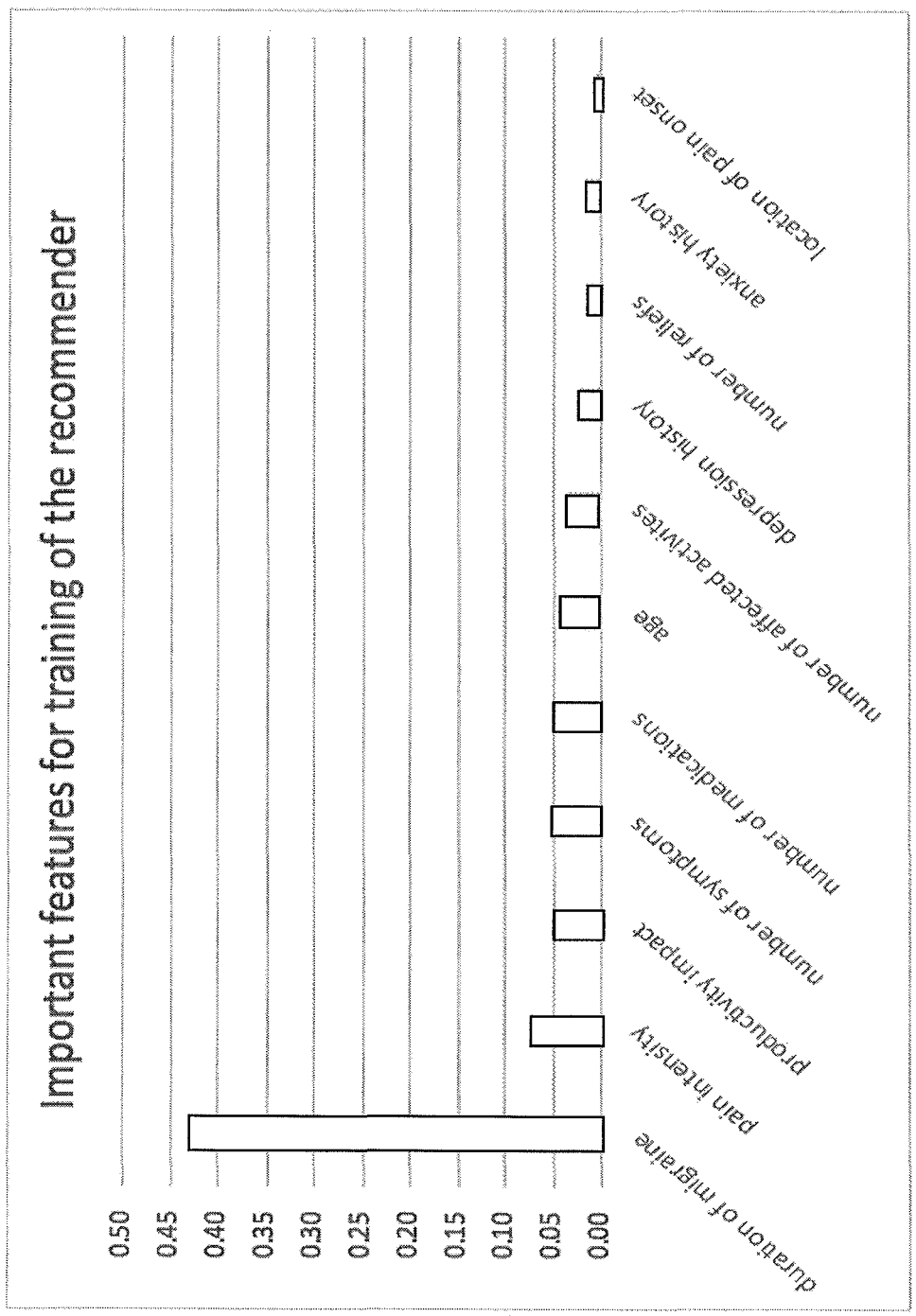
Figure 22:
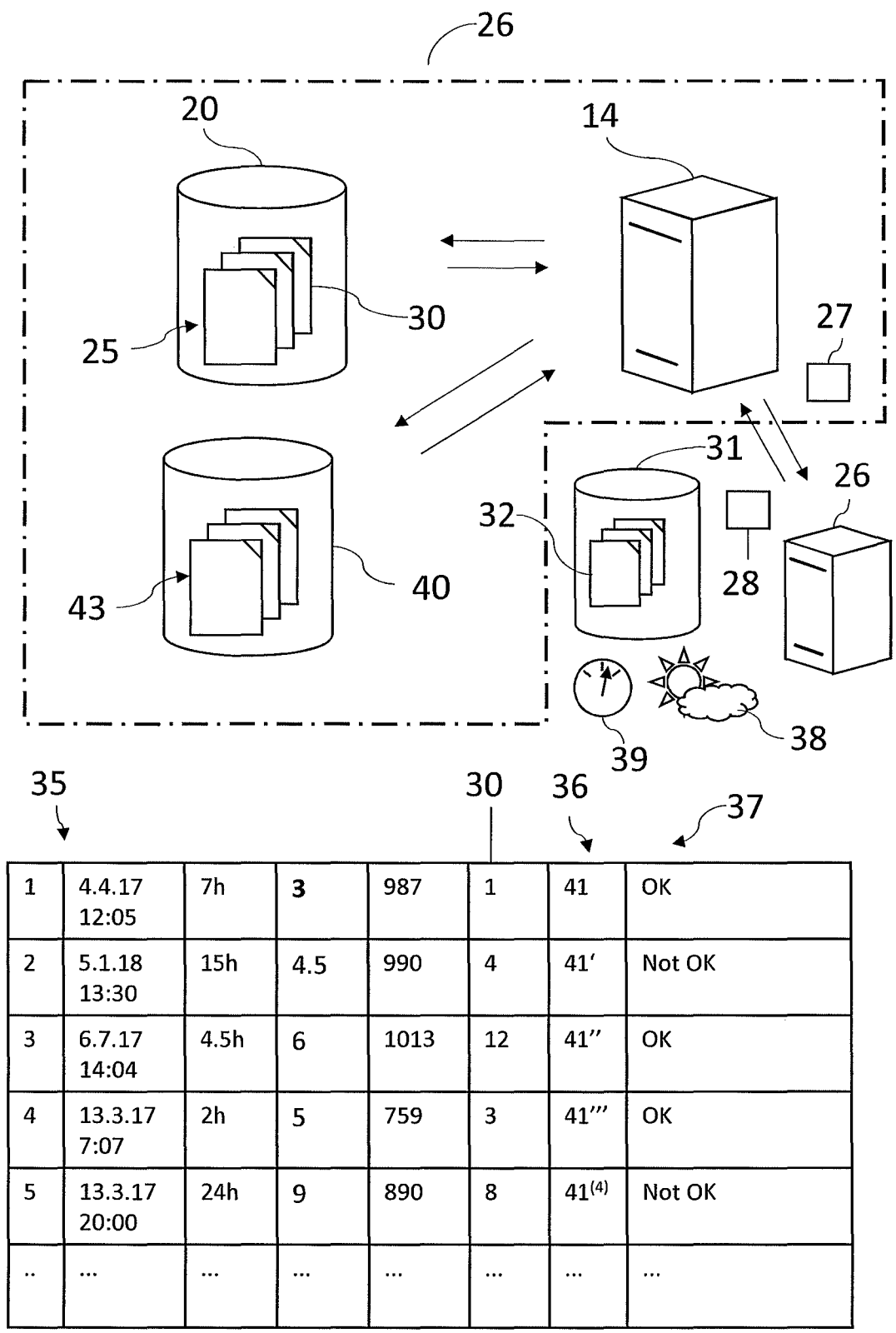
Figure 24:
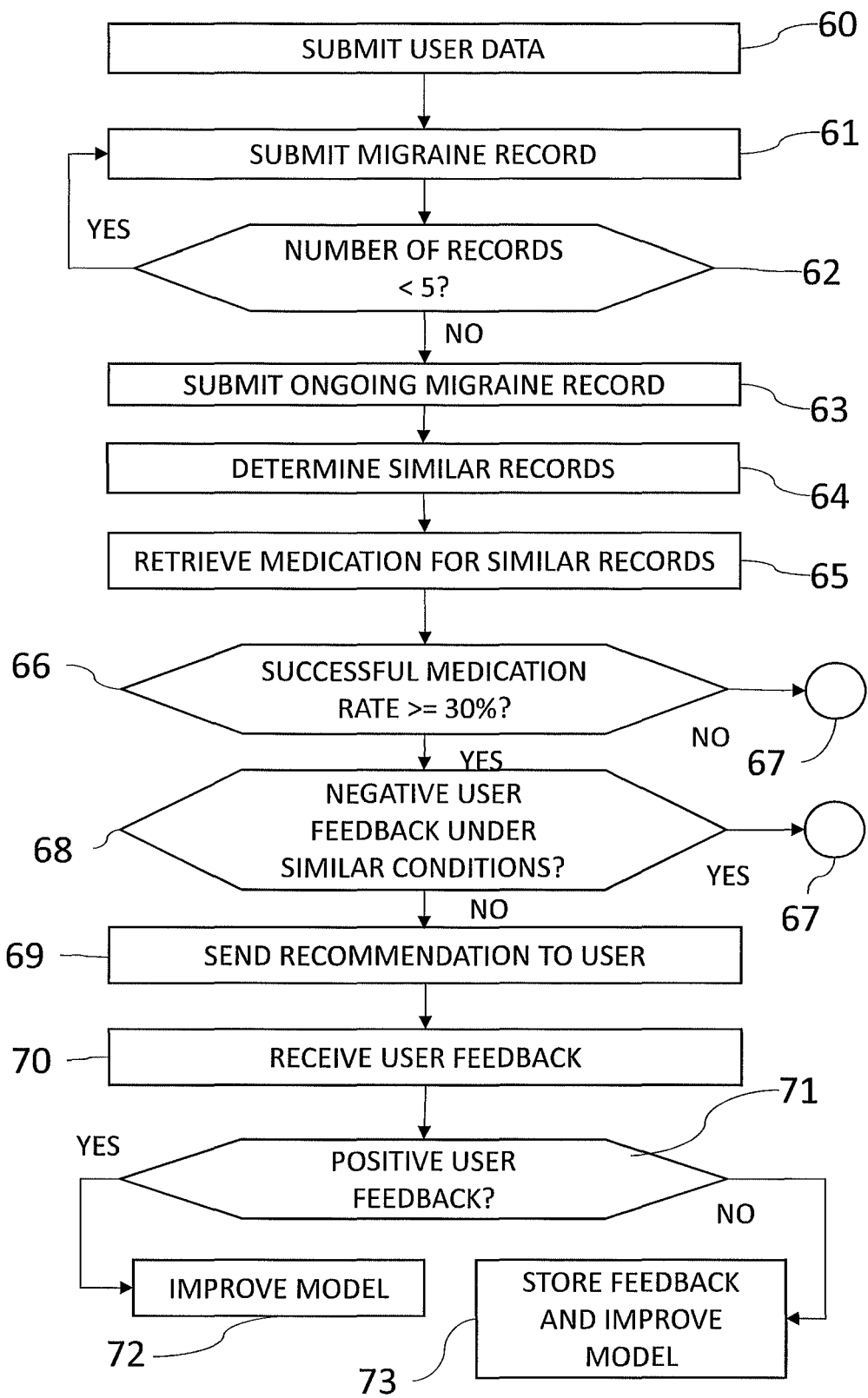

The subject matter of the present specification is now explained in further detail with reference to the following figures in which FIG. 1 shows a medication recommendation system, FIG. 2 shows a logistic function for use in a logistic regression of an output variable of the medication recommendation recommender of the system of FIG. 1, FIG. 3 shows a decision tree for deciding between medications A, B and C, FIG. 4 illustrates a random forest statistical algorithm used in the medication recommender, FIGS. 5 to 11 show an improvement of a gradient boosting algorithm of the system of FIG. 1 depending on a number of decision trees used, FIG. 12 shows an example of a neural network for use in the medication recommender, FIG. 13 shows an example of an evaluation of medications 1.1 to 3.4 by a user of the medication recommender, given the previous migraine records 1, 2 and 3, FIG. 14 illustrates a functioning of a spell checker of the medication recommender, FIG. 15 shows in further detail the functioning of the spell checker of FIG. 14, FIG. 16 shows a training data set used for training a statistical model of the medication recommender, FIG. 17 shows a balanced training data set obtained by undersampling, FIG. 18 illustrates the training of a stacked model of the medication recommender, and FIG. 19 illustrates the training of a stacked model of the medication recommender comprising a random forest, a neural network and a gradient boost model, FIG. 20 shows a comparison of five performance metrics for random forest, XGBoost, neural network procedures and for a stacking of these three procedures, FIG. 21 shows a list of relevant factors/features used in the training of the medication recommender, FIG. 22 shows a more detailed view of server-side components of the medication recommendation system of FIG. 1, FIG. 23 shows examples of data hosed on the server-side components of FIG. 22, and FIG. 24 shows a process for providing a medication recommendation to an end user and for updating the recommendation process.

FIG. 1 shows a medication or drug recommendation system 10 which comprises portable electronic devices, such as mobile phones and laptops, a personal computer and a server. The portable electronic devices comprise a software application that provides user input from a user 19. In particular, the medication recommendation system 10 comprises mobile phones 11 with respective mobile phone applications that are capable of receiving input data from the user 19 through elements of a graphical user interface 15, through textual and graphical input and, optionally, through sensors 16 of the mobile or through external sensors 17 and 18.

The server 14 comprises a computer readable memory 5 with a computer readable program 6. The computer readable program 6 is capable of providing recommendations, and in particular a recommended medication, to the user 19 with the aid of a statistical model. Furthermore, the computer readable program 6 is able to adjust the statistical model to improve predictions or recommendations of the statistical model base on migraine event data on the database 20 and/or on migraine event data provided by the user 19 through a client device.

The server 14 is connected to a database 20 over a first communication link 21. The database 20 comprises medication related data, migraine related data and parameters of statistical models used in the mobile phone application 9. Furthermore, the server 14 is connected to the devices 11, 12, 13 over respective communication links 22, 23, 24.

The server 14 can exchange data with the devices 11, 12, 13. For example, the server 14 receives data from the users 19 which allows the server 14 to improve the quality of the statistical models used in respective software applications on the devices 11, 12, 13. During operation, the server 14 computes improved parameters of the statistical models, stores the improved parameters in the database 20 and sends the improved parameter data to the devices 11, 12, 13.

In FIG. 1, server data messages 7, such as recommendation messages and request messages, are indicated by at a server side of the communication links 22, 23, 24 and user data messages 8, such as user feedback messages and user response messages are indicated at a side of a user device. Furthermore, client applications 9, which run on the client devices 11, 12, 13 are indicated by application windows 9. The client applications 9 are also referred to as user applications.

A data synchronization in the drug recommendation system 10 can be carried out as described below. In this context "synchronization" refers to the concept of keeping data consistent among several devices or storage media. Data synchronization keeps datasets coherent and maintain their integrity across several data storage media. Network errors, loss of network, and using multiple devices are some of the causes of a loss of synchronization.

In the drug recommendation system 10, synchronization is used to maintain integrity between the server, the devices and the database, to allow up-to-date data for the model training and ensure accurate outcome delivered to the user device.

A loss of synchronization is defined as the state where the data of a single user is not perfectly similar in each of his devices, and in the server 14. For example, the user 19 may have entered migraine data into the mobile phone 15 but not into the laptop 12. Synchronization makes sure the user's data appears the same on all his devices 15 and 12, regardless of which device he used to enter the data.

The server 14 ensures there is no loss of synchronization, by propagating each change in data to each component of the system: database and each user device. To this effect, the server 14 prevents concurrent migraines to be recorded by the same user, independently of the number of devices. A minimum threshold between two migraines is chosen as a suitable time interval, such as one minute.

If the server 14 faces a synchronization error that it can not solve automatically, it will send a message to the user, via one of the connected devices. The message will prompt the user and ask him which version of the migraine should be kept, and which one should be discarded.

FIG. 2 shows a logistic function for use in a logistic regression of an output variable of the medication recommender of the system of FIG. 1.

Logistic regression is one of the most widely used fundamental classification model. The logistic function, which is a sigmoid function, has the form of $$\sigma(t)=\exp(t)/(1+\exp(t))=1/(1+\exp(-t)).$$

It takes any real value as input and outputs a value between 0 to 1. If there is a binary classification problem, σ(t) is considered as the probability of an event that has an outcome as 1.

According to the logistic regression model, a conditional probability to obtain a positive decision under the condition that the n Variables $X_1, \ldots, X_n$ take on the values $x_1, \ldots, x_n$ is given by:

$$P(X_1=x_1, \ldots, X_n=x_n)=\exp(\beta_0+\beta_1 x_1+\ldots+\beta_n x_n)/(1+\exp(\beta_0+\beta_1 x_1+\ldots+\beta_n x_n)).$$

wherein the parameters $\beta_0, \ldots, \beta_n$ are determined by the logistic regression. This corresponds to the case in which the variable t in the logistic function is a linear combination of the explanatory variables $X_i$. If the values $x_1, \ldots, x_n$ are given, the conditional probability can be evaluated, which leads to a prediction that Y takes on the value 1 when P>0.5 and that Y takes on the value 0 when P<0.5.

In particular, Y=1 can correspond to a case in which a migraine medication A is recommended and Y=0 can correspond to a case in which the migraine medication A is not recommended.

In the following, several statistical models are described, which can be used in the medication recommender, namely decision tree, random forest, XGBoost and sequential neural networks. Other statistical models may be used as well, especially models which are similar to the ones described below.

FIG. 3 shows, by way of example, a decision tree 50 for use in the medication recommender. In the example of FIG. 3, recommendations of medications A, B, C correspond to the respective leaves of the tree. The decision tree splits into different branches at a male/female decision and at the age thresholds 20 years and 40 years. These branching criteria are provided by way of illustration only. The criteria can be pre-determined or they can also be modified or adjusted by a learning procedure.

Decision tree is one of the most frequently used supervised machine learning algorithm that can be applied to both regression and classification problems. It mimics the decision-making process of human brains. It grows from a root (base condition), when it meets a condition (internal node/feature), it splits to multiple branches. The end of the branch that does not split anymore is an outcome (leaf).

A decision tree can be generated using a training data set as described below:
1. Starting from a root node (the entire dataset), the algorithm splits the dataset in two branches using a decision rule or branching criterion
2. Each of these two branches generates a new child node
3. For each new child node, the branching process is repeated until the dataset cannot be split any further
4. Each branching criterion is chosen to maximize information gain. Herein, "information gain" is a quantification of how much a branching criterion reduces uncertainty in the children nodes and "uncertainty" is a quantification of how mixed the labels are. The labels are the data or the classification that is predicted by the decision tree.

FIG. 4 illustrates a random forest classification, which includes a random forest 51. The random forest 51, which is also referred to as random forest model, is an ensemble of decision trees 50', 50", 50'" with randomly selected features in each decision tree 50', 50", 50'" so that it can provide more stable and accurate outcomes. Outcomes are determined by majority voting in the case of a classification problem.

In the example of FIG. 4, a random forest model, which has been trained previously by a training method, is used to decide between classifications A, B and C. For example, a random forest with only the three decision trees shown in FIG. 4 would return the classification A by majority voting.

FIGS. 5 to 11 illustrate an XGBoost method. XGBoost, or eXtreme Gradient Boosting, has become very popular due to its use in a large number of competitions since its publication 4 years ago. Boosting is an ensemble technique to improve the performance by adding new models on top of prior models. Gradient boosting uses gradient descent algorithm to create new models on residuals of prior models.

XGBoosting is a type of gradient boosting, which is a machine learning technique for regression and classification problems, which produces a prediction model in the form of an ensemble of weak prediction models, typically decision trees. It builds the model in a stage-wise fashion, like other boosting methods, and it generalizes them by allowing optimization of an arbitrary differentiable loss function.

The XGBoost and Random forest models are similar in that both of them are ensembles or collections of decision trees. So once created, they predict in the same way, by averaging the results of all the trees in the ensemble.

The difference between them is the way they are trained. XGBoost uses an additive strategy.
1. Train a decision tree
2. Compute the difference (residual) between the prediction and the actual value/ground truth
3. Save the residual errors, use them as the label for the next training
4. Repeat until a target number of trees is created
Random forest uses a random strategy
1. Select randomly k features from the total number of features
2. Create a tree from these k features using the same process as for a decision tree
3. Repeat a target number of trees is created The XGBoost method is an example of a boosting method. Different from the Random Forest method, in which many decision trees are optimized independently and the prediction is an average of decision tree output values, the XGBoost method generates successive decision trees from preceding iterations and the a prediction is obtained from of decision tree output values.

The iterations that lead to the result curves of FIGS. 5 to 11 of the XGBoost method can be represented in the following pseudocode:
1. Randomly select a subsample of features and instances x_1, and fit a model (Tree 1): $F_1(x_1)=y_1$
2. Calculate the residuals $e_1$, and fit a new model: $h_1(x_1)=e_1$
3. Combine the previous models to make a new model (Tree 2): $F_2=F_1+h_1$
4. Get another random subsample $x_2$, calculate the residuals: $e_2=F_2(x_2)-y_2$
5. Repeat steps 3 and 4 and get new models.

In summary,
$$F_1+h_1=F_2 \longmapsto F_3=F_2+h_2 \longmapsto \ldots \longmapsto F_k=F_{(k-1)}+h_{(k-1)}$$

Herein, "residual" refers to a difference between values of a test dataset and predicted values, which are predicted from a training dataset. In the case of a numerical variable the residual is the arithmetic difference.

In the case of a categorical variable, such as "male" and "female", the variable is first transformed into a numerical value before the residual is calculated. By way of example, the transformation can be done using a "one hot encoding" in which a variable is set to 1 if it belongs to a given category and to 0 otherwise.

More precisely, the XGBoost method uses a gradient of a loss function, which measures a difference between the predicted values and the values of the test data set, to compute the residual. Further information about XGBoost can be found for example in the document arXiv: 1603.02754v3 on the arXiv.org document server of Cornell University.

During each iteration, the task is to train a model based on the residuals. Then the new model will be created by combining the new residual model and the model in the last iteration. Hence, the predictors in each iteration are not independent, but sequential.

Both random forest and XGBoost are ensemble algorithms that have a collection of predicted results which come together to make a final decision. However, there are some significant differences between these two algorithms.

Firstly, random forest uses bagging, which means there are a collection of independent models that will generate a collection of results, and the final decision will be made by combining these results. In contrast, XGBoost uses boosting which is sequential. Results of each iteration depends on the previous results.

Moreover, due to the different algorithms that these models adopt, they handle different issues while training the models. Random forest mainly aims to improve the accuracy by reducing the variance. On the other hand, XGBoost reduces both bias and variance. However, it is more common for XGBoost to overfit without an early-stopping criterion. By using a stacking method to the present specification, which includes both of these models as input, the strengths of both methods can be combined. The stacking method is explained further below.

FIG. 12 shows a sequential neural network 53. Originally inspired by biological neural networks, an artificial neural network may comprise multiple layers, with numerous neurons in each layer. Layers other than the input layer and the output layer are referred to as hidden layers. In each hidden layer, neurons receive weight-adjusted inputs from the previous layer, then perform transformation by a non-linear activation function, and finally generate outputs for the next layer.

In the example of FIG. 12, the inputs are labelled as feature 1 to feature 5 and the outputs are labelled as output 1 and output 2.

A sequential neural network, such as the one shown in FIG. 12, is a simple neural network model, which has a linear stack of layers (Keras Google group, 2015). The sequential neural network is also referred to as a feed forward neural network. The sequential neural network of FIG. 12 has an input layer, two hidden layers and an output layer. The output of the individual nodes in the output layer can be interpreted as a 0/1, or YES/NO decision of a classification, either directly or after applying a suitable threshold.

A supervised training of the neural network can be achieved by adjusting the weights based on a training dataset. For example, a gradient descent learning rule, such as a Widrow-Hoff learning rule, or a back-propagation learning rule could be used to train the network of FIG. 12.

The medication recommendation system makes use of user data to train and to improve the statistical models used. This is further illustrated by the data provided below. The data was provided by users of the Migraine Buddy smartphone application (MB) from the United States, Great Britain, Canada and Australia who have recorded outcomes (helpful/unhelpful) of migraine medication molecules and are selected as training samples.

The user data can comprise, by way of example, the date and time a migraine started, the date and time a migraine ended, the type of headache the patient experiences, the intensity of the migraine pain, the part of head where pain started, a list of aura symptoms reported by the patient, a list of symptoms reported by the patient (other than aura symptoms), a list of migraine triggers, a list of activities affected by the migraine, a list of activities reported by the patient to relieve his migraine (e.g. sleep, etc.), an outcome of medications and reliefs reported by the patient, and the place where migraine pain started.

FIG. 13 shows an example of user data provided by the smartphone users. Features are selected from three different granularities, namely user-level, migraine-level and molecule-level. One user can have multiple migraine records, with several medications possibly consumed in each record, as shown in FIG. 13.

The medication recommender makes use of statistical models to predict whether a molecule would be helpful (classes), and to quantify the degree of helpfulness (probability). These models consider all recorded molecules as input. To accomplish this, columns acting as a big matrix are created as features, as shown in Table 1 below:

TABLE 1

| Samples of molecule columns | |
|---|---|
| Migraine_id | Molecule |
| 1 | ibuprofen |
| 2 | acetaminophen |
| ... | ... |
| k-1 | sumatriptan |
| k | ketoprofen |

| Migraine_id | ibuprofen | acetaminophen | sumatriptan | ... | ketoprofen | sum |
|---|---|---|---|---|---|---|
| 1 | 1 | 0 | 0 | 0 | 0 | 1 |
| 2 | 0 | 1 | 0 | 0 | 0 | 1 |
| ... | 0 | 0 | 0 | 1 | 0 | 1 |
| k-1 | 0 | 0 | 1 | 0 | 0 | 1 |
| k | 0 | 0 | 0 | 0 | 1 | 1 |

In the following, a processing of input data for obtaining a training dataset and a test dataset is explained in further detail. The training dataset and the test dataset are then used for adjusting parameters of computational statistical models used by the medication recommender of the medication recommendation system of FIG. 1. The processing includes the processing steps of data pre-processing, extract relevant data from a database, balance a training dataset by under-sampling.

1. Preprocessing in Database

Raw data are recorded in different tables of a relational database, for example of a PostgreSQL Databases.

It is advantageous to process data before extracting it from databases for future usage, because most raw data contain inaccuracies and inconsistencies, including but not limited to misspelling and abbreviation. Molecule matching and spell check algorithms are applied to modify and process raw data.

a. Molecule Matching

The molecule matching algorithm aims to output the active ingredient when there is a medication as input. The input may be misspelled, abbreviated and/or contain extraneous information in the form of note taking. The algorithm looks to isolate relevant information, search in multiple dictionaries and find the correct form, and return the active ingredient.

In total, three major data sources for medications were used:

i. Migraine Buddy's (MB) databases that have users' records, ii. Third party reference Drug Database (DD) to deal with new medications that haven't been recorded in Migraine Buddy's databases and iii. Manually-created dictionary to deal with special cases such as abbreviations.

The following Table 2 shows samples of molecule matching results, which were obtained by processing an input text and matching the processed text with dictionary entries according to the above-mentioned process. In Table 2, "MB" denotes "Migraine Buddy", "DD" denotes "Drug Database" and "customized" denotes a customized database.

| Input | Problem | Dictionary Source | Output |
|---|---|---|---|
| Ibruprophen | Misspelling | MB's Databases | Ibuprofen |
| Ibuprofen tablets | Stop words | MB's Databases | Ibuprofen |

-continued

| Input | Problem | Dictionary Source | Output |
|---|---|---|---|
| Frovex | New Abbreviation | DD's Databases | Frovatriptan |
| Ibu | Abbreviation | Customized | Ibuprofen | b. Spell Check

The spell check algorithm aims to correct free text of users' inputs to proper English words. This algorithm is applied to medical items such as triggers and symptoms so that they can be categorized and applied in models.

The majority of users' inputs belongs to less than 6-word sentences. Spell checking algorithm is based on the similarity and edit distance between strings. There are three basic principles that this algorithm follows:

1. choose the nearest/most similar one among all alternative candidates,
2. when two candidates are tied (or nearly tied), i.e. the same edit distance or similar similarity score, choose the most common one (Manning, Raghavan, & Schutze, 2008) and
3. choose the longest candidate when varied length candidates available.

As illustrated in FIG. 14, the first step of the procedure is cleaning text, which involves removing punctuations and special characters and splitting only relevant text into words. Then a list of words is passed to the function that performs a search for exact match. The matched results will be saved, and the unmatched text will be passed to another function that performs match based on similarity scores and edit distance. Within each match function, the function will look for the longest match with diminishing length until there is no more match available. A simple example is shown in FIG. 15.

c. Categorization Algorithm

There are more than 122,000 distinct triggers and 61,000 distinct symptoms recorded on the Migraine Buddy platform. To reduce dimensions and avoid similarities between items, categorization is necessary by matching with key words.

2. Extract Relevant Data from Database

SQL is used to query relevant data from databases on the airflow platform. Extracted data are loaded as pandas DataFrames. Then feature engineering and combinations of DataFrames are processed via Python. Missing values are filled as either median of the column if it's numeric or the most frequent item appeared in that column if it's not numeric. For example, if a user did not indicate gender, this user will be considered as a female since more than 90% of Migraine Buddy users who report a gender are female.

3. Balance Training Dataset by Under-Sampling

Next, the acquired dataset is separated as a training data set (33) and a test dataset (34), which are represented by columns in FIG. 16. The training data set is also referred to as "training database" and the test data set is also referred to as "test database".

At that time, the proportion of test dataset is 10% of original dataset. However, 80% of training records were found to have positive outcomes, with the rest negative.

To solve this unbalancing issue, under-sampling is applied by randomly selecting the same number of records as minority class from the majority class. The effect of under-sampling is illustrated in FIGS. 16 and 17. After processing, both classes have the same number of instances in the training dataset.

4. Process Data for Respective Models

Different models have different requirements for input datasets. The medication recommender takes this into account by transforming the input data before providing the data as input to a procedure that implements a statistical model.

In the case of basic models, such as logistic regression and decision tree, and for ensemble models such as random forest and XGBoost, categorical features are first transformed into dummy variables. The dummy variables are then provided as input data to the respective basic or ensemble model.

In the case of a sequential neural network model, additional processes are performed, including feature standardization, as disclosed for example in "Pedregosa, et al., 2011" and converting labels to binary class matrix, as disclosed for example in "Keras Google group, 2015".

Features are standardized by subtracting its mean and dividing its standard deviation according to the following formula:

$$f(x) = \frac{x - \bar{x}}{\sigma(x)}$$

Finally, after under-sampling, the training dataset contains about 200,000 records. A test dataset is created by randomly selecting about 1/5 records of the original data set.

According to a specific embodiment, the medication recommender makes use of supervised learning, wherein the supervised learning uses statistical models that are selected from the following five supervised models, which can be categorized according to the following three model categories:

1. Linear model: logistic regression,
2. Tree-based models: decision tree, random forest, and XGBoost and
3. Neural Network: sequential neural network.

FIGS. 18 and 19 illustrate a stacking method 58 or stacking model 58. Stacking is an ensemble technique which has two levels aiming to improve the performance. Unlike sequential and parallel ensemble methods, which use the same base algorithm, this technique combines multiple base algorithms via a meta-algorithm. (Smolyakov, 2017). At level 0, models with different base algorithms are trained based on a level-0 training dataset. Then the outputs from level-0 are treated as features and a simple meta-algorithm will be trained to generate the final prediction.

In particular, the statistical models can be provided by the abovementioned models, as illustrated in FIG. 19.

Stacking (sometimes called stacked generalization) involves training a learning algorithm to combine the predictions of several other learning algorithms. First, all of the other algorithms are trained using the available data, then a combiner algorithm or beta model 56 is trained to make a final prediction using all the predictions of the other algorithms as additional inputs.

If an arbitrary combiner algorithm is used, then stacking can represent many different ensemble techniques, although, in practice, a logistic regression model is often used as the combiner. Stacking typically can yield a performance that is better than any single one of the trained models.

FIG. 19 provides a more specific example of a stacking method 58', in which the statistical models 53, 54, 55 of FIG. 18 are provided by a random forest model 51, an XGBoost model 57 and a sequential neural network model 52, and in which the beta model 56 is provided by a logistic regression 56'.

By applying the above-mentioned stacking technique, using random forest, XGBoost and neural network as base models at level 0, and applying a logistic regression model at level 1, the accuracy improves further to 0.83. The improvement is illustrated in FIG. 20.

The following table 3 illustrates the improved accuracy achieved by stacking the random forest, XGBoost and sequential neural network algorithms using a logistic regression method. As shown in Table 3, a stacking by using logistic regression generates higher accuracy than random forest, XGboost and sequential neural network on their own.

TABLE 3

Result of stacking

| Algorithms | Test accuracy |
|---|---|
| Random Forest | 0.7876 |
| XGboost | 0.8001 |
| Sequential Neural Network | 0.7643 |
| Stacking | |
| Logistic regression | 0.8300 |

Based on the test accuracy, among standalone models, random forest model and XGBoost model perform the best. These results can be further improved by applying stacking to combine the predictions of random forest, XGBoost, and neural network models.

The prediction improvement was obtained for the specific test data, models and model parameters of the above-mentioned example and it can be expected that an improved prediction is in general achieved with a medication recommender using the above-mentioned statistical models and a stacking of those models, at least in the sense that an improved prediction is achieved on average or in a majority of use cases. In general, machine learning methods are able to make satisfactory predictions of outcomes of medications.

The results demonstrate that ensemble techniques such as random forest and XGBoost yield a much better performance than simple models such as logistic regression and decision tree. However, the sequential neural network generated a worse result than ensemble methods, which can be attributed to overfitting or to the simple 2-hidden-layer structure applied in this example. With a small number of hidden layers in the neural network model, it is less likely to generate new hidden features to improve the performance.

The confusion matrices for the top performers are displayed in Table 4.1-4.4. The relevant metrics are plotted in FIG. 20.

TABLE 4.1

Random forest confusion matrix

|   | 1 | 0 |
|---|---|---|
| 1 | 36,455 | 10,548 |
| 0 | 1,974 | 9,973 |

TABLE 4.2

XGboost confusion matrix

|   | 1 | 0 |
|---|---|---|
| 1 | 37,124 | 9,879 |
| 0 | 1,860 | 10,087 |

TABLE 4.3

Neural Network confusion matrix

|   | 1 | 0 |
|---|---|---|
| 1 | 35,240 | 11,763 |
| 0 | 2,131 | 9,816 |

TABLE 4.4

Confusion matrix after stacking

|   | 1 | 0 |
|---|---|---|
| 1 | 12,029 | 2,109 |
| 0 | 898 | 2,649 |

FIG. 20 shows a comparison between metrics of model performance. All four techniques have similar true positive rates (as known as recall) which is higher than 0.9, suggesting that there are more than 90% chances of being correct when the real label is positive. However, these techniques have various false positive rates as well as specificity. The sequential neural network has the lowest specificity, and it performs the worst among the techniques in terms of accuracy. This suggests that when the real labels are negative, these techniques do not perform as accurate as the scenario when the real labels are positive. The precision is the highest after applying stacking, which also leads to the highest accuracy. It is suggesting that the model is reliable when the prediction is positive.

The most important features used to training the recommender are shown in FIG. 21 where it is shown that the durations of migraines (duration in seconds) play a significant role in the recommender training, in addition to other features like pain intensity, age, and the number of symptoms experienced during a migraine.

The following tables 5.1 and 5.2 show, by way of example, a performance of statistical models. In table 5.1 the statistical models have default parameters.

| Model | Default test accuracy |
|---|---|
| Logistic regression | 0.64 |
| Decision tree | 0.78 |
| Random forest | 0.81 |
| XGboost | 0.82 |
| Sequential neural network | 0.81 |

Table 5.2 shows the performance of statistical models after parameter tuning.

| Model | Best Estimators | Parameters Discussion | Result |
|---|---|---|---|
| Logistic regression | C = 0.6<br>Fit_intercept = False<br>Penalty = 'l1'<br>Solver = 'liblinear'<br>Tol = 0.0001 | C: inverse of regularization strength; the smaller the value is, the stronger the regularization effect is.<br>Fit_intercept: specifies if a bias should be added to the decision function. | 0.87 |

-continued

| Model | Best Estimators | Parameters Discussion | Result |
|---|---|---|---|
| | | Penalty: specifies the norm used in the penalization. Solver: specifies the solver usee in the optimization problem Tol: tolerance for stopping criteria. (Pedregosa, et al., 2011) | |
| Decision tree | Criterion = 'entropy' Max_depth = 100 Min_impurity_decrease = 0.0001 Min_samples_leaf = 1 Min_samples_split = 8 Splitter = 'best' | Criterion: the function to measure the quality of a split. 'entropy' represents information gain. Max_depth: the maximum depth of the tree. Min_impurity_decrease: threshold to determine whether a node will be split. Min_sample_split: The minimum number of samples required to split an internal node. Splitter: the strategy used to choose the split at each node. 'best' is to choose the best split. (Pedregosa, et al., 2011) | 0.88 |
| Random forest | Bootstrap = False Criterion = 'gini Max_depth = None Min_impurity_decrease = 0.0 Min_samples_leaf = 1 Min_samples_split = 2 N_estimators = 800 | Bootstrap: determines whether to bootstrap samples when building trees. Criterion: same as decision tree. 'Entropy' represents information gain. Max_depth: same as decision tree. Min_impurity_decrease: same as decision tree. Min_sample_leaf: the minimum number of samples required to be at a leaf node. Min_sample_split: The minimum number of samples required to split an internal node. N_estimators: determines number of trees in the forest. (Pedregosa, et al., 2011) | 0.95 |
| XGBoost | Booster = 'gbtree' Colsample_bytree = 0.8 Gamma = 0.01 Learning_rate = 0.1 Max_depth = 12 N_estimators = 500 Reg_alpha = 0 Reg_lambda = 0.85 Subsample = 0.8 | Booster: which technique to train the new models. Colsample_bytree: subsample ratio of columns when constructing each tree. Gamma: Minimum loss reduction required to make a further partition on a leaf node of the tree. Learning rate: step size shrinkage used in update to prevents overfitting. Max_depth: same as decision tree. Reg_alphal: L1 regularization term on weights. Reg_lambda: L2 regularization term on weights. Subsample: subsample ratio of the training instances. (Chen & Guestrin, 2016) | 0.96 |
| Sequential eural network | portion = 1 optimizer = 'adam' init_mode = 'he_uniform' epochs = 500 dropout_rate = 0.05 batch_size = 10,000 activation = 'sigmoid' | Portion: number of neurons in each layer = portion * number of features Optimizer: 'adam' is an algorithm for first-order gradient-based optimization of stochastic objective function. (Kingma & Ba, 2014) Init_mode: initializers that define the way to set the initial random weights of Keras layers. (Keras Google group, 2015) 'he_uniform': He uniform variance scaling initializer. (He, Zhang, Ren, & Sun, 2015) | 0.92 |

| Model | Best Estimators | Parameters Discussion | Result |
|---|---|---|---|
| | | Dropout_rate: the percentage of training sample to be randomly dropped from the neural network during training. (Srivastava, Hinton, Krizhevsky, & Ilya Sutskever, 2014) Epochs: 1 epoch = 1 forward pass + 1 backward pass of the entire training examples. (Keras Google group, 2015) Batch_size: defines number of samples that going to be propagated through the network. (htttps://stats.stackexchange.com/users/64943/itdxer), 2016) Activation: activation functions transform linear inputs to non-linear outputs. 'sigmoid' represents standard logistic function. (R, 2017) | |

FIG. 22 shows a view of server-side components 26 of the medication recommendation system of FIG. 1. The server components comprise the server 14, the databased 20 and a medication database 40.

The database 20 stores user data 25, which comprises user data sets 30. Each of the user data sets 30 comprises migraine event data 35, recommendation data 36 and outcome data 37, which are illustrated in the table at the bottom of FIG. 22. The recommendation data, which include a medication, are labeled as 41', 41", 41''', 41$^{(4)}$ in FIG. 22.

The migraine data 35, comprise a duration of the migraine event, an intensity of the migraine event on a 1-10 scale, a pressure at a start of a migraine event, and a pressure variation data during the migraine event, wherein the pressure is measured in millibar or hectopascal. In particular, the pressure variation can be a maximum pressure variation during the past 12 hours before a reporting time of the migraine event or before the start of the migraine event. The migraine event data may also comprise further data, for example other migraine contributing factors such as amount of sleep, drug consumption, menstruation etc.

The medication database 40 comprises medication data 43, which are shown in FIG. 23.

The server 14 is furthermore configured to communicate with a weather server 26 and retrieve data from the weather server 26 by sending request messages 27 and receiving response messages 28. The weather server 26 is connected to a weather database 31, which comprises time dependent data 32, such as weather data 32. The weather data is obtained by measuring environment variables of an environment 38, such as pressure and temperature, with an environment sensor 39.

For example, the weather data can comprise an atmospheric pressure upon a start time of a migraine attack, a maximum pressure variation in the previous 12 hours before a migraine attack start time for a location that is automatically reported or confirmed by a user device.

In a more general embodiment, the weather server is an external server which comprises time dependent and/or location dependent data, which can be retrieved using time and/or location data from users of the medication recommendation system 10.

FIG. 23 shows examples of data that is stored on the server-side components 26 of FIG. 22.

A medication data table 42, which is stored in the medication database 40, comprises information about excluded medication for a user. In another embodiment, the exclusion of the medication depends on conditions of a migraine event submitted by the user or on other conditions and these conditions may be stored in the same table 42 or in another linked table.

The medication data sets 43 comprise, among others, a medication ID, a medication name, an active molecule content in milligram, a list of associated complications, a list of associated indications, a provider ID of the medicament and previous success rate of the medicament.

The data of the databases 20, 31 and 40 of FIG. 1, such as the data shown in the tables of FIGS. 1, 22 and 23 may be stored in table form or in other data structures, such as data objects, XML data structures and so forth. The respective data, such as medication data may be stored in one table or data structure or in multiple tables or data structures which are linked with each other, for example by key values.

FIG. 24 shows a process for providing a medication recommendation to an end user and for updating the recommendation process.

In a step 60, user data of a user is transmitted form a client device to a server. In a further step 61, a migraine record of the user is transmitted from the client device to the server. A number of submitted user records of the user device is counted in a step 62.

If the submitted user record exceeds a minimum count, which is set to 5 migraine records in the example of FIG. 24, a server program uses a migraine record which relates to an ongoing migraine episode and which is transmitted from the client device to the server in a step 64, to provide a recommendation.

In a step 65, medications which were prescribed for similar records are retrieved. In other words, the data sets are filtered according to similarity criteria. Among others, similar migraine records can determined by determined by an exact match or by a match within a pre-determined range, such as migraine records submitted for the same contributing factor or for the same age group.

If the server program finds one or more medications among the previously identified medications that have had at least a predetermined success rate, such as a minimum of 30%, the server program selects one of the medications according to a predetermined criterium in a step 66. For example, the citerium can be a combination of success rate and previous price, such as success_rate—weighting_factor*price. If the server program does not find a medication with a successful medication rate among the similar data sets, the process terminates in a step 67.

Furthermore, the server program retrieves user data of the user to which the recommendation is being provided in a step 68. The user data comprises previous migraine records and previously submitted recommendations to the user.

If the server program finds that the user data contains a negative user feedback for the selected medication, and that the selected medication was previously recommended under similar conditions as the currently submitted migraine record, the server program searches for a next best medication among the previously identified medications in step 68. If no such medication is found, the process terminates in the step 67.

In a further step 69, the recommended medication and/or other recommendations is transmitted from the server to the device of the user, for example over a wireless connection.

Furthermore, a request for user feedback is generated after a predetermined time or after data is received according to which the user has applied the recommended medication.

The request for user feedback is generated on the user device or it is generated on the server and is sent from the server to the user device. In a step 70, the server program receives a user feedback message. The statistical model for generating the generation is adjusted or improved in step 71 or in step 72. If the user feedback is negative, the negative feedback is stored on the server such that is linked to the user and to the migraine event for which the recommended medication is provided.

By storing the negative feedback, a recommended medication that received a negative user feedback can be excluded from a recommended medication, and a different medication can be chosen instead when the user reports another migraine event. Furthermore, the server can check whether the conditions provided by data of the reported migraine event are similar to the conditions reported with the migraine event that has received the negative feedback and only in this case exclude the previously recommended medication.

In particular, the prediction model may comprise a statistical model which can be adjusted based on the received user feedback. Among others, the statistical model may be provided by one of the previously described statistical models, such as a decision tree, an ensemble of decision trees, such as a random forest, a neural network or an XBoost method. The statistical model may also comprise one or more further classification methods with adjustable parameters, such as a support vector machine, a statistical model based on a principal component computation or others.

The adjustment of the statistical model or of the parameters of the statistical model, such as an adjustment of weights and/or connections of a neural network, and thereby improving an average prediction accuracy and/or an amount of positive user feedback is also referred to as "machine learning".

If the user feedback is negative, the user feedback is stored in a database of the server in order to avoid providing the medication which has caused the negative feedback under the same or similar conditions.

Furthermore, the user feedback the step 72 of improving the model may also comprise storing the positive user feedback.

A method for providing a medication according FIG. 24 can also be carried out according to the below mentioned steps.

Each Migraine Buddy user creates a unique account in order to use the app.

Each time the user hits a "Confirm" button in the app (there is a "Confirm" button at the bottom of each record screen and at the bottom of each settings screen), the app connects to the server and synchronizes the account data with the most recent changes, providing the device is connected to the internet. If the device is not connected to the internet, synchronization will take place next time a "confirm" button is hit while the device has internet access.

Data export and log out requests are only possible while the device has internet access, as both actions trigger a full synchronization with the server.

The user records the following optional data in Migraine Buddy:
  Profile (age, gender, etc.)
  Health history (preventive medication, other conditions, etc.)
  Settings (willingness to share information for research purpose, willingness to receive notifications etc.)
  Daily tracker (daily activities that may be trigger attacks)
  Sleep (daily sleep records)
  Attacks (migraines attacks with up to 14 tracked settings)
  Survey/questions answers (such as feedback survey on the efficiency of prior medication recommendations)

The medication recommendation engine requires a minimum of information in order to generate a recommendation:
  Profile (age, gender)
  Settings (authorization to analyze attack records in order to generate a recommendation, authorization to push a notification)
  5 completed migraine attack records Providing the above has been fully completed and synchronized with the server, let's assume that the user creates a sixth attack record on his Migraine Buddy app, while having internet access:
  Start date and no end date (meaning that the attack is ongoing) and confirms
  Attack type and confirms
  Pain intensity and confirms
  Pain onset and confirms
  Medication used and confirms
  Symptoms and confirms
  Aura and prodrome and confirms
  Location and confirms
  Menstruation and confirms
  Then confirms the record as ongoing by hitting the "Confirm" button.

This last action will trigger a synchronization of the attack record on the server, with status "ongoing". As all prior minimum information and authorizations on user account are met, the server will launch immediately the Medication recommendation engine for this user and attack.

The engine will retrieve the following data:
  Current attack duration based on start time and date
  Current attack type
  Current attack pain intensity
  Current attack pain onset
  Current attack used medication
  Current attack symptoms
  Current attack aura and prodrome
  Current attack menstrual period
  Weather information (pressure, humidity and temperature variations prior to attack start) from a weather data service provider, based on current attack's start time and location User profile (age, gender)

Last 5 attacks data: attack duration, attack type, pain intensity, pain onset, used medication, used medication relief scale, aura and prodrome, menstrual period, location)

Last 5 days of Daily tracker information (if available)

Last night's sleep record (if available)

History of user medication recommendation feedback (if available)

The engine will then pull similar records from similar users (age group, gender) in the hundreds of millions of attack records in the server and create a temporary table with these records.

Providing the table contains at least 1000 records, it will retrieve:

Every recommended medication fed back as useful

Every medication recorded as useful

If the most reported useful medication occurrence reaches 30%, which implies in the case of 1000 records that the medication has been reported as useful in 300 or more instances, then the medication recommendation engine checks whether this medication has already been recommended to the user in similar attack conditions. Providing no negative user feedback was given for this medication in similar attack conditions, the engine will return a positive result to the server with this medication, treatment and success frequency.

The server will subsequently generate a push notification to the user account, that will pop up immediately on every user device with internet access, on which Migraine Buddy app is installed and user account logged in.

The push notification message will be as such: "in similar conditions, MedX 10 mg is useful for 63% migraine buddy users. Hope you get well soon".

Once the server receives the confirmation that the attack record has been confirmed as ended (i.e. it has an end date and time and has been confirmed on the user's device, that synchronized the information back to the server), the server will send a push notification to the user, that will open a two-question survey:

Question 1: did you take the recommended medication? (YES/NO)

If the answer is YES, Question 2: was the medication helpful? (YES/NO)

The answers to the survey are sent to the server and added to the attack record as medication recommendation feedback. A medication that did not prove to be useful to the user will not be recommended again in similar conditions.

The following table 6 provides an example of migraine event data, which is used to generate a recommendation, in particular a recommended medication. Among others, the migraine event data can be provided by self-reported data which are input by a user on a client device by using an input form of an application that is installed on the client device, by sensors which are connected to the client device or the data can also be retrieved from the client device or from a server device over an internet connection. For example, values such as a wake up time or a blood pressure can be collected by sensors that are connected to a body of a user of the client device or the user of the client device can type in these data as input values.

| Name of variable | Reporting granularity | Description |
| --- | --- | --- |
| Date | Event | Reference date for all other variables |
| Migrain duration | Event | Recorded duration of migraine |
| Pain intensity | Event | Average pain level reported across migraine(s) recorded per user. Per migraine the records the highest pain level associated with the observed migraine. (0 for no-pain. 1-10 with the smileys, figures and functional impairment description). |
| Reports anxiety | Event | True if the patient reported anxiety at any point during the migraine recorded that day |
| Reports depression | Event | True if the patient reported depression at any point during the migraine recorded that day |
| Reports being affected at work | Event | True if the patient reported being affected at work (but not missing work) at any point during the migraine recorded that day |
| Reports missing work | Event | True if the patient reported missing work at any point during the migraine recorded that day |
| Reported location | Event | Name of reported location at time of the migraine |
| All reported triggers | Event | All triggers reported during the day, comma separated |
| All reported symptoms | Event | All symptoms reported during the day, comma separated |
| All reported auras | Event | All auras reported during the day, comma separated |
| All reported affected activities | Event | All affected activities reported during the day, comma separated |
| All reported medications and reliefs | Event | All affected medication & reliefs reported during the day, comma separated |
| All reported outcomes | Event | All affected outcomes reported during the day, comma separated [maps to the medication & reliefs, one by one, same order] |
| Nb of triggers | Event | Count of triggers reported by user across their migraine(s) recorded on that day |
| Nb of symptoms | Event | Count of symptoms reported by user across their migraine(s) recorded on that day |
| Nb of auras | Event | Count of auras reported by user across their migraine(s) recorded on that day |

-continued

| Name of variable | Reporting granularity | Description |
|---|---|---|
| Nb of affected activities | Event | Count of affected activities reported by user across their migraine(s) recorded on that day |
| Nb acute medication doses | Event | Nb of doses of acute medication taken |
| Nb unique acute medication molecules | Event | Count of unique medication molecules reported by user across their migraine(s) recorded per day |
| Nb otc doses | Event | Total doses of OTC medication taken by the patient on all migraines recorded that day |
| Nb triptans doses | Event | Total doses of Trptan medication taken by the patient on all migraines recorded that day |
| Nb opioids doses | Event | Total doses of opioids medication taken by the patient on all migraines recorded that day |
| Nb other RX doses | Event | Total doses of other RX medication taken by the patient on all migraines recorded that day |
| OTC outcome | Event | The helpfulness recorded by the subject for the OTC (scale: "helpful", "somewhat helpful" or "unhelpful"). If several molecules of a category were recorded, the average helpfulness value is given (values: "helpful" = 1.0, "somewhat helpful" = 0.5, "unhelpful" = 0.0). |
| Triptan outcome | Event | The helpfulness recorded by the subject for the Triptan (scale: "helpful", "somewhat helpful" or "unhelpful"). If several molecules of a category were recorded, the average helpfulness value is given (values: "helpful" = 1.0, "somewhat helpful" = 0.5, "unhelpful" = 0.0). |
| Opioids outcome | Event | The helpfulness recorded by the subject for the Opioid (scale: "helpful", "somewhat helpful" or "unhelpful"). If several molecules of a category were recorded, the average helpfulness value is given (values: "helpful" = 1.0, "somewhat helpful" = 0.5, "unhelpful" = 0.0). |
| Other RX outcome | Event | The helpfulness recorded by the subject for the Other RX (scale: "helpful", "somewhat helpful" or "unhelpful"). If several molecules of a category were recorded, the average helpfulness value is given (values: "helpful" = 1.0, "somewhat helpful" = 0.5, "unhelpful" = 0.0). |
| Pain position: Left Side | Event | True if the patient recorded pain on the left side of the head during that day, else False |
| Pain position: Right Side | Event | True if the patient recorded pain on the right side of the head during that day, else False |
| Start of prophylaxis treatment | Event | First record of a prophylactic molecule |
| Molecule of prophylaxis treatment | Event | Molecule used for prophylaxis |
| End of prophylaxis treatment | Event | User reports end of prophylaxis (non-report tracking) or no prophylaxis recorded for X months (3 month for anti-CGRP/Botox, 1 month for others). N/A if current treatment is on-going. |
| Weather: Atmospheric Pressure | 3 hours before event start to event start | Median in hPa (millibars) aggregated from per minute data |
| Weather: Temperature | 3 hours before event start to event start | Median in C aggregated from per minute data |
| Weather: Relative Humidity | 3 hours before event start to event start | Median in % (relative humidity) aggregated from per minute data |
| Acceleration Sensor: X-axis in m/s2 | 3 hours before event start to event start | Median aggregated from per minute data |

-continued

| Name of variable | Reporting granularity | Description |
|---|---|---|
| Acceleration Sensor: Y-axis in m/s2 | 3 hours before event start to event start | Median aggregated from per minute data |
| Acceleration Sensor: Z-axis in m/s2 | 3 hours before event start to event start | Median aggregated from per minute data |
| Sleep: Wake up time | Event | Time of wake up, in the patient's local time |
| Sleep: Variation with usual wake up time | Event | Time of wake up – Average Time of wake up (past 3 months) |
| Sleep: Duration | Event | Duration of sleep in hours during the previous night |
| Sleep: Nb of interruptions | Event | Number of interruptions throughout sleep |

The embodiments can also be described with the following two lists of elements being organized into items, which can be combined with the embodiments of the specification.

1. A recommendation system for rating of medications for migraine based on self-reported data, capable of suggestion, prediction, and ranking of outcome of migraine medications on case by case basis.
2. The recommendation system of item 1, wherein the medication can be administered using any of the common routes including enteral, parenteral and topical routes.
3. The recommendation system of item 1, wherein self-reported data is collected from data, the data being collected worldwide and stored on a central repository database server.
4. The recommendation system of item 3, wherein the mode of collection can be either active reporting through a form or passive acquisition through a sensor.
5. The recommendation system of item 1, wherein the recommendation system comprises a recommendation engine, the recommendation engine making use of data processing, the data processing comprising machine learning models.
6. The recommendation system according to item 5, wherein input parameters to the recommendation engine include combinations of symptoms, triggers, demographics, environment parameters, previous drug outcome.
7. The recommendation system of item 5, wherein the data processing includes a molecule matcher, a spell checker and a categorizer.
8. The recommendation system of item 7, wherein an input medication of the molecule matcher is translated into an active ingredient through use of a drug dictionary, previous input data, a custom dictionary or a combination thereof.
9. The recommendation system of item 7, wherein the spell checker corrects the misspelled words based on similarity and edit distance.
10. The recommendation system of item 7, wherein the categorizer categorizes symptoms, triggers and other medical terms.
11. The recommendation system of item 5, wherein the recommendation engine comprises machine learning models, the machine learning models comprising a stacking with XGBoost, Random Forest, and sequential neural networks techniques.
12. The recommendation system of item 5, wherein a prediction accuracy increases iteratively upon arrival of more new data records.

1. A recommendation system for prediction and ranking of medications for migraine based on self-reported data, the recommendation system comprising
   a server device, the server device comprising a server database,
   a client computer device, with an environment sensor for measuring an environment variable, with a computer memory, the computer memory comprising a recommendation application and a client database, and with a communication means for communicating with the server device over a communication link,
   the recommendation application being operative to receive self-reported data of a user of the client computer device over a user interface of the recommendation application, to receive environment data from the environment sensor, and to retrieve user-specific data from the client database,
   to generate a recommendation request message, the recommendation request message comprising the self-reported data, the environment data, and the retrieved user-specific data,
   to send the recommendation request message over the communication link, using the communication means, wherein the server device is operative
   to receive the recommendation request message,
   to retrieve recommendation related data from the server database,
   to derive a recommendation within a pre-determined request response time, the deriving of the recommendation comprising applying at least one statistical procedure to the input data to obtain recommendation output data, the input data comprising data of the recommendation request message and the recommendation related data,
   the at least one statistical procedure comprising at least one of a random forest method, a gradient boost method and a sequential neural network method, the server device further being operative
   to generate a recommendation response message, the recommendation response message comprising the recommendation output data, to send the recommendation response message to the client device over the communication link.
2. The recommendation system of item 1, wherein the server device is operative to collect self-reported data from a multitude of other users from different countries and to store the self-reported data in the server database.
3. The recommendation system according to item 2, wherein the server device is operative to transmit model data to the mobile device, such that a prediction accuracy of the medication recommendation is enhanced, wherein the model data is derived from the collected self-reported data of the multitude of other users.
4. The recommendation system of one of the items 1 to 3, wherein the mode of collection comprises active reporting through a form of the recommendation application and/or passive acquisition through a sensor of the at least one environment sensor.
5. The recommendation system of one of the items 1 to 4, wherein the client computer device is further operative to identify and display a recommended form of administration of a migraine medication, the form of administration being selected from enteral, parenteral and topical routes of administration.
6. The recommendation system of item 5, wherein the client computing device can be a mobile computer device or a wearable computer device or any non-mobile computing device or alike.
7. The medication recommendation system of one of the items 1 to 6, wherein the input data to the at least one statistical procedure comprises symptoms, triggers, demographics, environment, or previous drug outcome of the user, or a combination thereof.
8. The medication recommendation system according to one of the items 1 to 7, wherein the client device is further operative to process the self-reported data, wherein the data processing comprising one or more of molecule matching, spell checking, and categorizing symptoms, triggers, medical terms and medications.
9. The recommendation system according to one of the items 1 to 8, wherein the client computer device or the server device is operative to translate an input medication provided by a user of the mobile computer device into an active ingredient, through use of drug dictionary, previous self-reported data, a custom dictionary, or a combination thereof.
10. The recommendation system according to one of the items 1 to 8, wherein the client computer device is operative, through use of a spell checker, to correct misspelled words of the self-reported data based on similarity and edit distance in relation to stored words in MB database, or drug database, or a combination thereof.
11. The recommendation system according to one of the preceding items 1 to 10, wherein the mobile device is operative to categorize symptoms, triggers and other medical terms by comparison with data in the client database and/or the server device.
12. The recommendation system according to one of the preceding items 1 to 11, wherein the machine learning models include stacking with XGBoost, Random Forest, sequential neural networks techniques, or a combination thereof.
13. The recommendation system according to one of the preceding items 1 to 12, wherein the server device is operative to synchronize user data between different devices, the synchronizing comprising determining a time overlap between user data relating to a first migraine event and a second migraine event and determining, based on the time overlap, whether the first migraine event and the second migraine event corresponds to the same migraine event, and, if it is determined that the first migraine event and the second migraine event correspond to the same migraine event, merging the data of the first migraine event with the data of the second migraine event.
14. A recommendation method for a rating of medications for migraine based on self-reported data, the recommendation system comprising a server device, the server device comprising a server database, and a client computer device with an environment sensor for measuring an environment variable, with a computer memory, the computer memory comprising a recommendation application and a client database, and with a communication means for communicating with the server device over a communication link, the method comprising
receiving self-reported data of a user of the client computer device over a user interface of the recommendation application,
receiving environment data from the environment sensor, and
retrieving user-specific data from the client database,
generating a recommendation request message, the recommendation request message comprising the self-reported data, the environment data, and the retrieved user-specific data,
sending the recommendation request message over the communication link, using the communication means, receiving the recommendation request message, retrieving recommendation related data from the server database,
deriving a recommendation within a pre-determined request response time, the deriving of the recommendation comprising applying at least one statistical procedure to the input data to obtain recommendation output data, the input data comprising data of the recommendation request message and the recommendation related data,
the at least one statistical procedure comprising at least one of a random forest method, a gradient boost method and a sequential neural network method,
generating a recommendation response message, the recommendation response message comprising the recommendation output data,
sending the recommendation response message to the client device over the communication link.
15. The recommendation method of item 14, further comprising collecting self-reported data from a multitude of other users from different countries and to store the self-reported data in the server database.
16. The recommendation method of item 15, further comprising retrieving model data from the server database and transmitting model data to the mobile device, such that a prediction accuracy of the medication recommendation is enhanced, wherein the model data is derived from the collected self-reported data of the multitude of other users.
17. The recommendation method of one of the items 14 to 16, wherein a data collection comprises active reporting through a form of the recommendation application and/or passive acquisition through a sensor of the at least one environment sensor.
18. The recommendation method of one of the items 14 to 17, further comprising identifying and displaying a recommended form of administration of a migraine medication, the form of administration being selected from enteral, parenteral and topical routes of administration.

19. The recommendation method of item 18, wherein the client computer device is a mobile computer device or a wearable computer device.
20. The recommendation method of one of the items 14 to 19, wherein the input data to the at least one statistical procedure comprises symptoms, triggers, demographics, environment, or previous drug outcome of the user, or a combination thereof.
21. The recommendation method according to one of the items 14 to 20, further comprising processing the self-reported data, wherein the data processing comprising one or more of molecule matching, spell checking, and categorizing symptoms, triggers, medical terms and medications.
22. The recommendation method according to one of the items 14 to 21, wherein the client computer device or the server device is operative to translate an input medication provided by a user of the mobile computer device into an active ingredient, through use of drug dictionary, previous self-reported data, a custom dictionary, or a combination thereof.
23. The recommendation method according to one of the items 14 to 22, further comprising correcting, through use of a spell checker, misspelled words of the self-reported data based on similarity and/or edit distance in relation to stored words in the client database.
24. The recommendation method according to any one of the items 14 to 23, wherein the mobile device is operative to categorize symptoms, triggers and other medical terms by comparison with data in the client database and/or the server device.
25. The recommendation method according to any one of the items 14 to 24, wherein the machine learning models include stacking with XGBoost, Random Forest, sequential neural networks techniques, or a combination thereof.
26. The recommendation method according to one of the items 14 to 25, further comprising synchronizing user data between different devices, the synchronizing comprising determining a time overlap between user data relating to a first migraine event and a second migraine event and determining, based on the time overlap, whether the first migraine event and the second migraine event corresponds to the same migraine event, and, if it is determined that the first migraine event and the second migraine event correspond to the same migraine event, merging the data of the first migraine event with the data of the second migraine event.

Although the above description contains much specificity, these should not be construed as limiting the scope of the embodiments but merely providing illustration of the foreseeable embodiments. Especially the above stated advantages of the embodiments should not be construed as limiting the scope of the embodiments but merely to explain possible achievements if the described embodiments are put into practice. Thus, the scope of the embodiments should be determined by the claims and their equivalents, rather than by the examples given.

BIBLIOGRAPHIC REFERENCE

"Ricci, F., Rokach, L., & Shapira, B. (2011)": "Introduction to Recommender Systems Handbook", in Recommender Systems Handbook (pp. 1-35), Springer.
"Pedregosa, et al., 2011": Machine Learning in Python. Journal of Machine Learning Research, 2825-2830.
"Keras Google group, 2015": Keras Google group. (2015, June 7), "Keras: The Python Deep Learning library". Retrieved from Keras Documentation: https://keras.io/
"Chen & Guestrin, 2016": Chen, T., & Guestrin, C., 2016, "XGBoost: A Scalable Tree Boosting System", Proceedings of the 22nd ACM SIGKDD International Conference on Knowledge Discovery and Data Mining (pp. 785-794), San Francisco: ACM.
"Kingma & Ba, 2014": Kingma, D. P., & Ba, J. (2014), "Adam: A Method for Stochastic Optimization", arXiv: 1412.6980
"He, Zhang, Ren, & Sun, 2015": He, K., Zhang, X., Ren, S., & Sun, J. (2015), "Delving Deep into Rectifiers: Surpassing Human-Level Performance on ImageNet Classification", arXiv:1502.01852
"Srivastava, Hinton, Krizhevsky, & Ilya Sutskever, 2014": Srivastava, N., Hinton, G., Krizhevsky, A., Ilya Sutskever, R. Salakhutdinov (2014), "Dropout: A Simple Way to Prevent Neural Networks from Overfitting", Journal of Machine Learning Research 15 (2014), pages 1929-1958.
"Smolyakov, 2017": Smolyakov, V. (22 Aug. 2017), "Ensemble Learning to Improve Machine Learning Results", retrieved from Stats and Bots: https://blog.statsbot.co/ensemble-learning-d1dcd548e936
"Manning, Raghavan, & Schutze, 2008": Manning, C. D., Raghavan, P., & Schutze, H. (2008), "Introduction to Information Retrieval", Cambridge University Press.

| | |
|---|---|
| 5 | computer readable memory |
| 6 | computer readable program |
| 7 | server data message |
| 8 | user data message |
| 9 | user application |
| 10 | drug recommendation system |
| 11 | mobile phone, device |
| 12 | laptop, device |
| 13 | device |
| 14 | server |
| 15 | mobile phone |
| 16 | mobile phone sensors |
| 17 | external sensor |
| 18 | external sensor |
| 19 | user |
| 20 | database |
| 21 | communication link |
| 22 | communication link |
| 23 | communication link |
| 24 | communication link |
| 25 | user data |
| 26 | weather server/external server |
| 27 | request message |
| 28 | response message |
| 30 | user data set |
| 31 | external database |
| 32 | time dependent data |
| 33 | training data set |
| 34 | test data set |
| 35 | migraine event data |
| 36 | recommendation data |
| 37 | outcome data |
| 38 | environment conditions |
| 39 | environment sensor |
| 40 | medication database |
| 41 | medication recommendation |
| 42 | medication data table |
| 43 | medication data sets |
| 50, 50', 50", 50''' | decision tree |
| 51 | random forest |
| 52 | neural network |
| 53 | statistical model |
| 54 | statistical model |
| 55 | statistical model |
| 56 | beta model |
| 56' | logistic regression |

-continued

| 57 | XGBoost model |
| 58, 58' | stacking model |
| 60 | method step |
| 61 | method step |
| 62 | decision step |
| 63 | method step |
| 64 | method step |
| 65 | method step |
| 66 | decision step |
| 67 | termination step |
| 68 | decision step |
| 69 | method step |
| 70 | method step |
| 71 | decision step |
| 72 | method step |
| 73 | method step |

The invention claimed is:

1. A system comprising:
a data store comprising a program of instructions; and,
a processor operably coupled to the data store such that, when the processor executes the program of instructions, the processor causes health event prediction model operations to be performed to generate an environmentally-responsive therapy prediction, the operations comprising:
receive, via a first electronic message from a client device of a user, a first health event profile (HEP) comprising a first time corresponding to onset of a first health event of the user and a first location corresponding to a location of the user;
generate and transmit to a weather server a weather retrieval message (WRM) comprising the first time and the first location;
generate, in response to receiving from the weather server a weather message comprising a first atmospheric pressure corresponding to the first time and the first location, a first weather-enriched HEP comprising the first HEP and the first atmospheric pressure;
apply a medication recommendation model (MRM) to the first weather-enriched HEP to determine a recommended medication as a function of at least the first weather-enriched HEP and at least one historical outcome-enriched HEP, wherein each historical outcome-enriched HEP comprises a weather-enriched HEP corresponding to a historical health event, a corresponding recommended medication, and a corresponding indication whether the recommended medication was successful;
generate a recommendation message comprising the recommended medication;
generate a request message containing a first prompt for the user to input whether a medication was taken according to the recommendation message, and a second prompt for the user to input whether the medication was successful;
generate and store, in response to receiving from the client device an outcome message containing an outcome profile (OP) generated from user input in response to the request message, an outcome-enriched HEP comprising the weather-enriched HEP and the OP; and,
generate an adjusted MRM based on the outcome-enriched HEP.

2. The system of claim 1, the operations further comprising:
if the OP corresponds to input from the user, in response to the second prompt, indicating that the medication was not successful, then generate and transmit to the client device for storage a medication non-recommendation message corresponding to the recommended medication.

3. The system of claim 1, the operations further comprising:
receiving a second HEP corresponding to a second health event from a second client device;
determining a first user identification (UID) from the first HEP and a second UID from the second HEP;
if the second UID is identical to the first UID, then:
determining from the first HEP a first health event end time, the first time being a first health event start time;
determining from the second HEP a second health event start time and a second health event end time;
if there is an overlap in time between the first health event and the second health event, then apply a data collision rule that prevents separate HEPs from being retained for the first health event and the second health event.

4. The system of claim 1, wherein:
the first HEP further comprises an environment profile generated from at least one environment sensor of the client device, and,
apply the MRM to the first weather-enriched HEP further determines the recommended medication as a function of the environment profile.

5. The system of claim 1, wherein:
the MRM comprises a decision tree, and,
generate an adjusted MRM includes adjustment operations comprising:
generate a training data set comprising a plurality of historical outcome-enriched HEPs, wherein each historical outcome-enriched HEP comprises a weather-enriched HEP corresponding to a historical health event, a corresponding recommended medication, and a corresponding indication whether the recommended medication was successful;
starting from a root node, split the training data set in two branches using a decision rule to generate a new child node for each of the two branches, wherein the decision rule is chosen to maximize an information gain; and,
for each new child node, repeat the split until the training data set cannot be split any further.

6. The system of claim 1, wherein:
the MRM comprises a decision tree,
the OP corresponds to input from the user, in response to the second prompt, indicating if the medication was successful, and,
generate an adjusted MRM includes adjustment operations comprising: generate updated values of branching criteria of nodes of the decision tree based on outcome-enriched HEP comprising the OP corresponding to the indication if the medication was successful.

7. The system of claim 1, wherein:
the MRM comprises a random forest, and,
generate an adjusted MRM includes adjustment operations comprising:
generate a training data set and a test data set, each comprising a corresponding plurality of historical outcome-enriched HEPs, wherein each historical outcome-enriched HEP comprises a weather-enriched HEP corresponding to a historical health event, a corresponding recommended medication, and a corresponding indication whether the recommended medication was successful;
generate a random forest MRM using the training data set; and,
apply the random forest MRM to the test data set to determine an accuracy of the random forest MRM.

8. The system of claim 1, wherein:
the MRM comprises a gradient boosting trees model, and,
generate an adjusted MRM includes adjustment operations comprising:
  (a) generate a training data set comprising a plurality of historical outcome-enriched HEPs, wherein each historical outcome-enriched HEP comprises a weather-enriched HEP corresponding to a historical health event, a corresponding recommended medication, and a corresponding indication whether the recommended medication was successful;
  (b) generate a first adjusted MRM fitting the training data set;
  (c) determining a first difference between a predicted output of the adjusted MRM and a ground truth of the training data set;
  (d) generate a first new model fitting the first difference;
  (e) generate a second adjusted MRM as a sum of the first adjusted MRM and the first new model;
  (f) repeating steps (c)-(e) until a predetermined accuracy of prediction between the predicted output and the ground truth is reached;
  (g) determining a second difference between the predicted output of the second adjusted MRM and the training data set;
  (h) generate a second new model fitting the second difference; and,
  (i) generate the adjusted MRM as a sum of the second adjusted MRM and the second new model.

9. The system of claim 1, wherein:
the MRM comprises a gradient boosting trees model, and,
generate an adjusted MRM includes adjustment operations comprising:
  generate a training data set comprising a plurality of historical outcome-enriched HEPs, wherein each historical outcome-enriched HEP comprises a weather-enriched HEP corresponding to a historical health event, a corresponding recommended medication, and a corresponding indication whether the recommended medication was successful; and,
  generate a sequence of decision trees by sequence generation operations comprising:
    (a) generate a first decision tree fitting the training data set;
    (b) apply the first decision tree to the training data set to generate an output of the first decision tree;
    (c) determine a first difference between the training data set and the output of the first decision tree;
    (d) determine a loss function from the first difference;
    (e) determine a gradient of the loss function;
    (f) determine a second decision tree as a function of the gradient;
    (g) generate a first adjusted MRM as a sum of the output of the first decision tree and an output of the second decision tree; and,
    (h) repeating steps (c)-(g) until a predetermined accuracy of prediction between the training data set and the output of the first decision tree is reached.

10. The system of claim 1, the operations further comprising generate a health event prediction model.

11. The system of claim 1, wherein the first health event comprises a neurological disease event.

12. The system of claim 11, wherein the neurological disease event comprises a migraine event.

13. The system of claim 1, wherein the first HEP comprises a migraine event profile (MEP).

14. The system of claim 1, the operations further comprising transmit, to the client device, at least one of: the recommendation message and the request message.

15. A computer-implemented method performed by at least one processor to generate an environmentally-responsive therapy prediction, the method comprising:
  receive, via a first electronic message from a client device of a user, a first health event profile (HEP) comprising a first time corresponding to onset of a first health event of the user and a first location corresponding to a location of the user;
  generate and transmit to a weather server a weather retrieval message (WRM) comprising the first time and the first location;
  generate, in response to receiving from the weather server a weather message comprising a first atmospheric pressure corresponding to the first time and the first location, a first weather-enriched HEP comprising the first HEP and the first atmospheric pressure;
  apply a medication recommendation model (MRM) to the first weather-enriched HEP to determine a recommended medication as a function of at least the first weather-enriched HEP and at least one historical outcome-enriched HEP, wherein each historical outcome-enriched HEP comprises a weather-enriched HEP corresponding to a historical health event, a corresponding recommended medication, and a corresponding indication whether the recommended medication was successful;
  generate a recommendation message comprising the recommended medication;
  generate a request message containing a first prompt for the user to input whether a medication was taken according to the recommendation message, and a second prompt for the user to input whether the medication was successful;
  generate and store, in response to receiving from the client device an outcome message containing an outcome profile (OP) generated from user input in response to the request message, an outcome-enriched HEP comprising the weather-enriched HEP and the OP; and,
  generate an adjusted MRM based on the outcome-enriched HEP.

16. The method of claim 15, further comprising generate a health event prediction model.

17. The method of claim 15, wherein the first health event comprises a neurological disease event.

18. The method of claim 17, wherein the neurological disease event comprises a migraine event.

19. The method of claim 15, wherein the first HEP comprises a migraine event profile (MEP).

20. The method of claim 15, further comprising transmit, to the client device, at least one of: the recommendation message and the request message.

21. A computer program product (CPP) comprising a program of instructions tangibly embodied on a non-transitory computer readable medium wherein, when the instructions are executed on a processor, the processor causes health event prediction model operations to be performed to generate an environmentally-responsive therapy prediction, the operations comprising:

receive, via a first electronic message from a client device of a user, a first health event profile (HEP) comprising a first time corresponding to onset of a first health event of the user and a first location corresponding to a location of the user;

generate and transmit to a weather server a weather retrieval message (WRM) comprising the first time and the first location;

generate, in response to receiving from the weather server a weather message comprising a first atmospheric pressure corresponding to the first time and the first location, a first weather-enriched HEP comprising the first HEP and the first atmospheric pressure;

apply a medication recommendation model (MRM) to the first weather-enriched HEP to determine a recommended medication as a function of at least the first weather-enriched HEP and at least one historical outcome-enriched HEP, wherein each historical outcome-enriched HEP comprises a weather-enriched HEP corresponding to a historical health event, a corresponding recommended medication, and a corresponding indication whether the recommended medication was successful;

generate a recommendation message comprising the recommended medication;

generate a request message containing a first prompt for the user to input whether a medication was taken according to the recommendation message, and a second prompt for the user to input whether the medication was successful;

generate and store, in response to receiving from the client device an outcome message containing an outcome profile (OP) generated from user input in response to the request message, an outcome-enriched HEP comprising the weather-enriched HEP and the OP; and, generate an adjusted MRM based on the outcome-enriched HEP.

22. The CPP of claim 21, the operations further comprising generate a health event prediction model.

23. The CPP of claim 21, wherein the first health event comprises a neurological disease event.

24. The CPP of claim 23, wherein the neurological disease event comprises a migraine event.

25. The CPP of claim 21, wherein the first HEP comprises a migraine event profile (MEP).

26. The CPP of claim 21, the operations further comprising transmit, to the client device, at least one of: the recommendation message and the request message.

* * * * *